(12) United States Patent
Dihora et al.

(10) Patent No.: US 11,794,161 B1
(45) Date of Patent: Oct. 24, 2023

(54) REDUCED PERMEABILITY MICROCAPSULES

(71) Applicant: TRUCAPSOL, LLC, Bethlehem, PA (US)

(72) Inventors: Jiten Dihora, Center Valley, PA (US); Praveen Bachawala, Allentown, PA (US)

(73) Assignee: TRUCAPSOL, LLC, Bethlehem, PA (US)

( * ) Notice: Subject to any disclaimer, the term of this patent is extended or adjusted under 35 U.S.C. 154(b) by 760 days.

(21) Appl. No.: 16/682,862

(22) Filed: Nov. 13, 2019

Related U.S. Application Data

(60) Provisional application No. 62/770,251, filed on Nov. 21, 2018.

(51) Int. Cl.

| | |
|---|---|
| B01J 13/16 | (2006.01) |
| C11D 17/00 | (2006.01) |
| A61K 9/50 | (2006.01) |
| A01N 25/28 | (2006.01) |
| A23L 2/00 | (2006.01) |
| A23L 27/00 | (2016.01) |

(52) U.S. Cl.
CPC ........... *B01J 13/16* (2013.01); *C11D 17/0039* (2013.01); *A01N 25/28* (2013.01); *A23L 27/72* (2016.08); *A61K 9/5026* (2013.01); *A61K 9/5073* (2013.01)

(58) Field of Classification Search
CPC ...... B01J 13/16; C11D 17/0039; A23L 27/72; A01N 25/28; A61K 9/5026; A61K 9/5073
See application file for complete search history.

(56) References Cited

U.S. PATENT DOCUMENTS

| | | |
|---|---|---|
| 3,345,358 A | 10/1967 | Inklaar |
| 3,819,838 A | 6/1974 | Smith et al. |
| 3,870,542 A | 3/1975 | Ida et al. |
| 4,076,774 A * | 2/1978 | Short ................... B41M 5/165 264/4.7 |
| 4,626,471 A | 12/1986 | Chao |
| 5,015,527 A | 5/1991 | Chao |
| 5,227,446 A | 7/1993 | Denzinger et al. |
| 5,550,189 A | 8/1996 | Qin et al. |
| 5,574,179 A | 11/1996 | Wahl et al. |
| 5,601,760 A | 2/1997 | Rosenberg |
| 5,837,747 A | 11/1998 | Soon-Shiong et al. |
| 6,248,909 B1 | 6/2001 | Akimoto et al. |
| 6,465,016 B2 | 10/2002 | Parikh et al. |
| 6,572,919 B2 | 6/2003 | Westland et al. |
| 6,596,073 B1 | 7/2003 | Nyssen et al. |
| 6,855,335 B2 | 2/2005 | Seok et al. |
| 7,431,986 B2 | 10/2008 | Van Lengerich et al. |
| 8,900,492 B2 | 12/2014 | Pacorel et al. |
| 8,900,495 B2 | 12/2014 | Pacorel et al. |
| 8,993,041 B2 | 3/2015 | To et al. |
| 9,205,395 B2 | 12/2015 | Yan |
| 9,332,774 B2 | 5/2016 | Nakhasi et al. |
| 9,416,050 B2 | 8/2016 | Seidl et al. |
| 9,427,719 B2 | 8/2016 | Viaud-Massuard et al. |
| 9,714,397 B2 | 7/2017 | Feng et al. |
| 9,937,477 B2 | 4/2018 | Zhang et al. |
| 9,944,886 B2 | 4/2018 | Hitchcock et al. |
| 9,993,401 B2 | 6/2018 | Barnett et al. |
| 10,188,593 B2 | 1/2019 | Dihora et al. |
| 11,179,302 B2 | 11/2021 | Dardelle |
| 11,344,502 B1 | 5/2022 | Dihora et al. |
| 11,542,392 B1 | 1/2023 | Multari |
| 11,571,674 B1 | 2/2023 | Dihora et al. |
| 2002/0169233 A1 | 11/2002 | Schwantes |
| 2004/0017017 A1 | 1/2004 | Van Lengerich et al. |
| 2004/0033264 A1 | 2/2004 | Sawhney |
| 2005/0272628 A1 | 12/2005 | Meli et al. |
| 2005/0276831 A1 | 12/2005 | Dihora et al. |
| 2008/0085297 A1 | 4/2008 | Dave et al. |
| 2008/0103265 A1 | 5/2008 | Schocker et al. |
| 2008/0167188 A1 | 7/2008 | Fischer et al. |
| 2009/0209661 A1 | 8/2009 | Somerville Roberts et al. |

(Continued)

FOREIGN PATENT DOCUMENTS

| | | |
|---|---|---|
| CA | 1049335 A | 2/1979 |
| CN | 114539887 A | 5/2022 |

(Continued)

OTHER PUBLICATIONS

Adhesives Magazine (2016). Sartomer: Acrylate Oliogmer. Available at: https://www.adhesivesmag.com/articles/94922-sartomer-acrylate-oligomer.

Leung et al. (2017). Enteric coating of micron-size drug particles through a Würster fluid-bed process. Powder Technology, 317, 247-252.

Silverajah et al. (2012). Mechanical, thermal and morphological properties of poly (lactic acid)/epoxidized palm plein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

(Continued)

*Primary Examiner* — Doan T Phan
(74) *Attorney, Agent, or Firm* — CAESAR RIVISE, PC

(57) ABSTRACT

Disclosed is a composition including controlled release particles, wherein each of the controlled release particles includes: (a) a core including at least one hydrophobic active ingredient; and (b) a wall at least partially surrounding the core and including: (i) an outer layer including a polyurea; (ii) an intermediate layer under the outer layer and including a carbamic-carboxylic anhydride; (iii) an inner layer under the intermediate layer and including an acrylate copolymer; and optionally (iv) an optional outer layer above the outer layer and including a quaternary amine containing moiety, wherein the viscosity of the core can be manipulated from a low viscosity liquid to a semisolid. A method for preparing the composition is also disclosed.

22 Claims, 5 Drawing Sheets

(56) References Cited

U.S. PATENT DOCUMENTS

| | | |
|---|---|---|
| 2010/0011610 A1 | 1/2010 | Bittorf et al. |
| 2010/0028451 A1 | 2/2010 | Kaplan et al. |
| 2011/0052680 A1 | 3/2011 | Hendrickson et al. |
| 2011/0268778 A1 | 11/2011 | Dihora et al. |
| 2011/0268802 A1 | 11/2011 | Dihora et al. |
| 2012/0128752 A1 | 5/2012 | Loo et al. |
| 2013/0004617 A1 | 1/2013 | Zhang et al. |
| 2013/0022654 A1 | 1/2013 | Deshmukh et al. |
| 2013/0084379 A1 | 4/2013 | Gregson et al. |
| 2013/0239429 A1 | 9/2013 | Vella et al. |
| 2014/0199244 A1 | 7/2014 | Rijcken et al. |
| 2014/0335032 A1 | 11/2014 | Panandiker et al. |
| 2014/0378369 A1* | 12/2014 | Barnett .................. A61Q 5/02 427/213.34 |
| 2015/0252312 A1 | 9/2015 | de Villeneuve et al. |
| 2016/0038428 A1 | 2/2016 | Harel et al. |
| 2016/0128944 A1 | 5/2016 | Chawrai et al. |
| 2016/0158121 A1 | 6/2016 | Lei et al. |
| 2016/0166480 A1 | 6/2016 | Lei et al. |
| 2016/0206561 A1 | 7/2016 | Kohane et al. |
| 2016/0228338 A9 | 8/2016 | Dihora et al. |
| 2017/0113200 A1* | 4/2017 | Zhang .................. A61K 9/50 |
| 2017/0165627 A1 | 6/2017 | Duan et al. |
| 2017/0216162 A1* | 8/2017 | Feng .................. B01F 23/00 |
| 2017/0360676 A1* | 12/2017 | Dihora .................. A61K 8/0241 |
| 2018/0015009 A1 | 1/2018 | Soubiran et al. |
| 2018/0042825 A1 | 2/2018 | Lei et al. |
| 2019/0275490 A1 | 9/2019 | Bachawala |
| 2021/0045409 A1 | 2/2021 | Witteveen et al. |
| 2021/0237018 A1 | 8/2021 | Bachawala et al. |
| 2021/0237019 A1 | 8/2021 | Bachawala et al. |
| 2021/0237020 A1 | 8/2021 | Bachawala et al. |
| 2022/0133603 A1 | 5/2022 | Bachawala et al. |
| 2022/0408771 A1 | 12/2022 | Dihora |
| 2023/0060181 A1 | 3/2023 | Dihora et al. |

FOREIGN PATENT DOCUMENTS

| | | |
|---|---|---|
| EP | 0076515 A1 | 4/1983 |
| EP | 0361677 B2 | 11/1993 |
| EP | 0815743 A2 | 1/1998 |
| EP | 1371410 A1 | 12/2003 |
| EP | 1797946 A2 | 6/2007 |
| WO | 9901214 A1 | 1/1999 |
| WO | 0105926 A1 | 1/2001 |
| WO | 03013538 A1 | 2/2003 |
| WO | 2004064971 A2 | 8/2004 |
| WO | 2006024411 A2 | 3/2006 |
| WO | WO 2006024411 A2 | 3/2006 |
| WO | 2007135583 A2 | 11/2007 |
| WO | 2008118133 A2 | 10/2008 |
| WO | 2009098226 A1 | 8/2009 |
| WO | WO 2009098226 A1 | 8/2009 |
| WO | 2011041395 A2 | 4/2011 |
| WO | 2015091877 A1 | 6/2015 |
| WO | 2016071151 A1 | 5/2016 |
| WO | 2017023830 A1 | 2/2017 |
| WO | 2020195132 A1 | 10/2020 |
| WO | WO 2020195132 A1 | 10/2020 |

OTHER PUBLICATIONS

English language abstract for WO 2020195132 A1 (2020).
http://polymerdatabase.com/polymer%20physics/sigma.html downloaded on Apr. 29, 2022.
Ko et al., "Characterization of hydrophilic-hydrophobic polymeric surfaces by contact angle measurements", Journal of Colloid and Interface Science, vol. 82(1) (1981).
OECD 301D method (OECD 1992, Test No. 301 Ready Biodegradability, OECD Guidelines for the Testing of Chemicals, Section 3, OECD Publishing, Paris, https://doi.org/10.1787/9789264070349-en.
Thakore et al. (2001). "Studies on biodegradability, morphology and thermo-mechanical properties of LDPE/ modified starch blends." European polymer journal, 37(1), 151-160.
U.S. Appl. No. 16/830,152, filed Mar. 25, 2020.
U.S. Appl. No. 16/853,003, filed Apr. 20, 2020.
U.S. Appl. No. 17/517,816, filed Nov. 3, 2021.
U.S. Appl. No. 16/776,828, filed Jan. 30, 2020.
U.S. Appl. No. 16/776,965, filed Jan. 30, 2020.
U.S. Appl. No. 16/777,048, filed Jan. 30, 2020.
U.S. Appl. No. 17/724,141, filed Apr. 19, 2022.
U.S. Appl. No. 17/724,166, filed Apr. 19, 2022.
U.S. Appl. No. 17/848,345, filed Jun. 23, 2022.
U.S. Appl. No. 17/861,204, filed Jul. 9, 2022.
U.S. Appl. No. 15/642,708, filed Jul. 6, 2017 (now abandoned).
U.S. Appl. No. 16/282,993, filed Feb. 22, 2019.
U.S. Appl. No. 16/287,509, filed Feb. 27, 2019.
U.S. Appl. No. 16/830,681, filed Mar. 26, 2020.
Luo et al., "Zein-Based Micro- and Nano-Particles for Drug and Nutrient Delivery: A Review", J. Appl. Polym. Sci., vol. 40696, 12 pages (2014).
International Search Report for PCT/US2017/037855, dated Nov. 2, 2017.
International Search Report for PCT/US2019/018959, dated Jul. 8, 2019.
U.S. Appl. No. 18/108,895, filed Feb. 13, 2023.
U.S. Appl. No. 18/112,781, filed Feb. 22, 2023.
Jardine. (2022). Amino-functionalized polysaccharide derivatives: Synthesis, properties and application. Current Research in Green and Sustainable Chemistry 5, 100309.
Gasparini et al. (2020). Quantification of residual perfume by Py-GC-MS in fragrance encapsulate polymeric materials intended for biodegradation tests. Molecules, 25, 718.
Larson et al. (2017). Bulky polar additives that greatly reduce the viscosity of concentrated solutions of therapeutic monoclonal antibodies. Journal of Pharmaceutical Sciences, 106, 1211-1217.
Guo et al. (2012). Structure-activity relationship for hydrophobic salts as viscosity-lowering excipients for concentrated solutions of monoclonal antibodies. Pharm Res, 3102-3109.
Kumar et al. (2017). Viscosity-reducing bulky-salt excipients prevent gelation of protein, but not carbohydrate, solutions. Appl Biochem Biotechnol, 1491-1496.
Wang et al. (2021). Hofmeister effect on the viscosity properties of gelatin in dilute solutions. Colloids and Surfaces B: Biointerfaces, 206, 111944.

\* cited by examiner

FIG. 4A
FIG. 4B
FIG. 5A
FIG. 5B
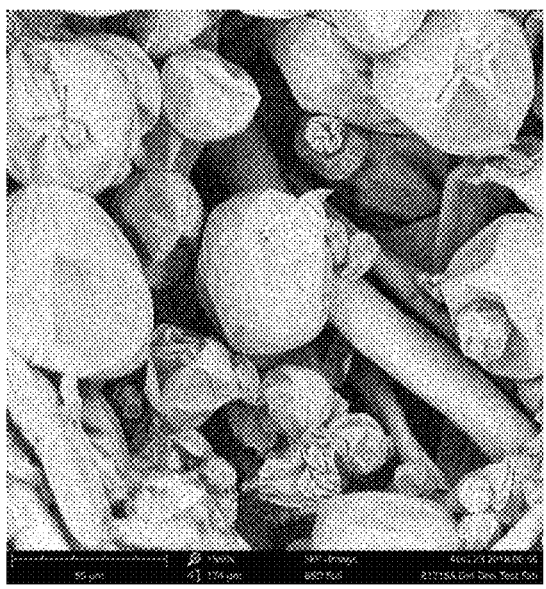

REDUCED PERMEABILITY MICROCAPSULES

BACKGROUND OF THE INVENTION

1. Field of Invention

This invention relates to controlled release compositions, encapsulation compositions and methods for making and using them.

2. Description of Related Art

There are many microencapsulated delivery systems disclosed in the art to control the release of the encapsulated active, or provide release when a specific trigger is applied. Such systems have previously suffered from a number of drawbacks.

Controlled release microcapsules that provide release of active upon application of shear or friction generally suffer from several drawbacks: (1) such microcapsules cannot be formulated in certain classes of products due to strict regulatory requirements, (2) they have high permeabilities when incorporated into products that contain high levels of surfactant, solvents, and/or water, which results in the premature benefit agent release, (3) they can only effectively encapsulate a limited breadth of benefit agents, (4) they either are so stable that they do not release the benefit agent in use or have insufficient mechanical stability to withstand the processes required to incorporate them in and/or make a consumer product, (5) they do not adequately deposit on the surface that is being treated with consumer product that contains capsules, and/or (6) they have a poor environmental biodegradability profile.

Such microcapsules are made via chemical processes that require the development of a membrane at the oil-water interface. Said membrane can be developed from the oil side or the water side, or both. An emulsion comprising the active material (dispersed phase) is stabilized in a continuous phase. In one mode, a shell material is deposited from the continuous phase onto a dispersed phase via precipitation of the shell material. In another mode, the shell material is manufactured within the dispersed phase, and migration of the shell material is induced via an interfacial reaction or insolubility of the shell material in the oil phase. The two approaches could be combined to develop "dual shell" capsules.

The permeability and the solubility parameter of this membrane determines the likelihood and the rate of diffusion of the encapsulated active out of the microcapsule. The solubility parameter of the membrane is determined by the choice of monomers that are reacted to form the shell material at the interface. Furthermore, the permeability of such shell material is determined by the crosslink density of the membrane. Polymers that are used to develop a membrane around the active material need to be crosslinked to provide a sufficient barrier to retain the encapsulated active until its desired release. However, a highly crosslinked membrane results in poor environmental biodegradability of the membrane.

Chemical processes utilized to manufacture controlled release microcapsules generally utilize thermal initiators—either in the aqueous phase or the lipophilic phase. High crosslink density of the shell material can be achieved at higher temperatures, for two reasons. First, there is a higher reactivity of the monomers at high temperature. Second, as the monomers react, the resulting polymer has a higher glass transition temperature. A higher reaction temperature results in higher mobility of the crosslinked polymer, providing a means to achieve a higher reactivity of the monomers to achieve a higher crosslink density. However, processing actives at higher temperatures can result in loss of the active, via evaporation or via thermal degradation. At low temperatures, such thermally initiated reactions require long batch cycle times, thus increasing the cost of the capsules. It is desired to complete these crosslinking reactions at lower temperatures in order to reduce the loss of volatile actives, and simultaneously achieve a degree of crosslinking that is sufficient to reduce the diffusion of the encapsulated active out of the microcapsule, in a time that does not significantly increase the cost of the microcapsules.

Conventional controlled release particles that comprise a core and a shell have several limitations. First, such capsules prematurely release the active material when suspended in a finished product formulations, such as cleaning product formulations. Second, such capsules have poor environmental biodegradability due to the nature of materials used and the degree of crosslinking that is achieved in order to reduce the diffusion of the active. Third, it is difficult to control the release profile of the encapsulated active. For example, the encapsulated material in the core is often a pool of liquid that pours out of the microcapsule and is absorbed by the surrounding substrate. Such absorption is undesired especially when the encapsulated active is a volatile material that is desired to be released into the surrounding environment. Such absorption is also undesired when it is desired the control the release of the active from the microcapsule over a long duration of time. Alternatively, the core can be a sponge or semisolid material that acts to restrict the diffusion of the encapsulated active, providing longevity of release of the volatile active but limited initial bloom of active material upon fracture of the capsule. Alternatively, it is desired to manipulate the viscosity of the core from a pool of liquid to a sponge or semisolid material. Fourth, poor adhesion of particles to the substrate result in significant loss of the particles, especially when formulations containing such particles are used in rinse-off applications.

Accordingly, it is desired to provide microcapsules that have lower permeability. Multiple membranes are developed around the core material to reduce the diffusion, and seal the pores.

It is further desired to improve the adhesion of particles to substrates in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water.

It is further desired to remove soil and dirt, but desired to retain active materials during the rinsing process by the retention of microcapsules on the substrate primarily via filtration.

It is further desired to provide a means to manipulate the release profile of the encapsulated active.

It is further desired to provide microcapsules that are processed at temperatures below 60° C., with a batch cycle time of less than 12 hours, and able to achieve a degree of crosslinking that is sufficient to reduce the diffusion of the encapsulated active out of the microcapsule.

Hence, it is desired to provide low permeability microcapsules that are able to retain the encapsulated active in surfactant containing solutions, or under highly dilute aqueous conditions. It is desired to improve the adhesion of microcapsules onto the desired substrate during rinse-off applications. It is desired to release the encapsulated active in larger quantities, and over a longer duration of time. It is desired to have capsules that have a favorable environmental biodegradability profile as defined by OECD 301D method.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

A first aspect of the invention is a composition comprising controlled release particles, wherein each of the controlled release particles comprises:
(a) a core comprising at least one hydrophobic active ingredient; and
(b) a wall at least partially surrounding the core and comprising:
  (i) an outer layer comprising a reaction product of an amine and an isocyanate;
  (ii) an intermediate layer under the outer layer and comprising a reaction product of an acid and an isocyanate;
  (iii) an inner layer under the intermediate layer and comprising an acrylate copolymer; and optionally
  (iv) an optional outer layer above the outer layer and comprising a quaternary amine containing moiety,
wherein the core is switchable from a low viscosity liquid to a semisolid without using high melting point waxes or polymers, and the controlled release particles are effective to retain the at least one hydrophobic active ingredient upon exposure to water and effective to release the at least one hydrophobic active ingredient in response to friction.

In certain embodiments, the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the amine is at least one member selected from the group consisting of linear aliphatic amines, aromatic amines, silicone amines, branched amines, polyamines and amino acids.

In certain embodiments, the isocyanate is at least one member selected from the group consisting of aliphatic isocyanates, aromatic isocyanates, polymeric isocyanates, cyclic isocyanates, hydrophilic isocyanates, hydrophobic isocyanates, waterborne isocyanates and urethane acrylates containing isocyanate functionalities.

In certain embodiments, the acid is an oil soluble acid monomer or oligomer comprising acid acrylates containing more than one carboxylic acid group, or a water soluble acid having more than one carboxylic acid group.

In certain embodiments, the acrylate copolymer is a member selected from the group consisting of ethylene glycol dimethacrylate, diethylene glycol dimethacrylate, aliphatic urethane diacrylates, aromatic urethane diacrylates, difunctional urethane acrylates, ethoxylated aliphatic difunctional urethane methacrylates, aliphatic urethane dimethacrylates, aromatic urethane dimethacrylates, epoxy acrylates, epoxymethacrylates, tetraethylene glycol dimethacrylate, polyethylene glycol dimethacrylate, 1.3 butylene glycol diacrylate, 1,4-butanediol dimethacrylate, 1,4-butaneidiol diacrylate, diethylene glycol diacrylate, 1.6 hexanediol diacrylate, 1.6 hexanediol dimethacrylate, neopentylglycol diacrylate, polyethylene glycol diacrylate, tetraethylene glycol diacrylate, triethylene glycol diacrylate, 1.3 butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, ethoxylated trimethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate.

In certain embodiments, the controlled release particles have a diameter from 0.1 microns to less than 200 microns.

In certain embodiments, the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

In certain embodiments, the composition further comprises at least one suspension agent to suspend the controlled release particles, wherein the at least one suspension agent is at least one member selected from the group consisting of a rheology modifier, a structurant and a thickener.

In certain embodiments, the at least one suspension agent has a high shear viscosity at, 20 sec$^{-1}$ shear rate and at 21° C., of from 1 to 7000 cps and a low shear viscosity, at 0.5 sec$^{-1}$ shear rate at 21° C., of greater than 1000 cps.

In certain embodiments, the composition is a fluid having a high shear viscosity, at 20 sec$^{-1}$ and at 21° C., of from 50 to 3000 cps and a low shear viscosity, at 0.5 sec$^{-1}$ shear rate at 21° C., of greater than 1000 cps.

In certain embodiments, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition comprises two different controlled release particles selected from the group consisting of friction-triggered release microcapsules which release the encapsulated active material at different rates due to the different in the viscosity of the core material.

In certain embodiments, the composition comprises two different controlled release particles selected from the group consisting of friction-triggered release microcapsules and water-triggered release microcapsules.

In certain embodiments, the at least one hydrophobic active ingredient comprises a mixture of a hydrophobic active and a material selected from the group consisting of brominated oils, epoxidized oils, highly nonpolar oils, hydrophobically modified inorganic particles, nonionic emulsifiers, oil thickening agents.

In certain embodiments, the composition has an Environmental Biodegradability greater than 30%.

In certain embodiments, the controlled release particles include the optional outer layer.

A second aspect of the invention is a method for preparing a composition of the invention, said method comprising the steps of:
(a) preparing an oil phase comprising the at least one hydrophobic active ingredient, at least one isocyanate, at least one acrylate, at least one initiator, at least one oil soluble acid, and optionally at least one acrylamide;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) reacting the at least one isocyanate with acidic monomers or oligomers or copolymers to form the intermediate layer comprising a carbamic-carboxylic anhydride;
(e) adding an amine moiety containing material at a stoichiometric ratio from 1:2 to 3:4 to react with the at least one isocyanate for 2-3 hours at room temperature to provide the outer layer;
(f) increasing a temperature at least 5° C. above an initiation temperature and reacting for 2 to 5 hours the at least one acrylate to provide the inner layer defining the core;
(g) adding surface modification agents to a suspension of the controlled release particles to improve adhesion between the particles and intended substrates; and
(h) adding structuring agents to the suspension of the controlled release particles to homogeneously suspend the particles in an aqueous dispersion.

A third aspect of the invention is a method for preparing a composition of the invention, said method comprising the steps of:
(a) preparing an oil phase comprising the at least one hydrophobic active ingredient, at least one isocyanate, at least one acrylate, at least one initiator, at least one oil soluble acid, and optionally at least one acrylamide;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) adding an amine moiety containing material at a stoichiometric ratio from 1:2 to 3:4 to react with the at least one isocyanate for 2-3 hours at room temperature to provide the intermediate layer;
(e) adding a water soluble acid and reacting for 2-3 hours at room temperature the at least one isocyanate with acidic monomers or oligomers or copolymers to form a carbamic-carboxylic anhydride outer layer;
(f) increasing a temperature at least 5° C. above an initiation temperature and reacting for 2 to 5 hours the at least one acrylate to provide the inner layer defining the core;
(g) adding surface modification agents to a suspension of the controlled release particles to improve adhesion between the particles and intended substrates; and
(h) adding structuring agents to the suspension of the controlled release particles to homogeneously suspend the particles in an aqueous dispersion.

In certain embodiments of the methods, the acrylamide is an alkylidene-bis-acrylamide where the alkylidene group has up to four carbon atoms.

In certain embodiments of the methods, the initiator is a member selected from the group consisting of peroxide, dialkyl peroxide, alkyl peroxide, peroxyester, peroxycarbonate, peroxyketone, peroxydicarbonate, 2,2'-azobis (isobutylnitrile), 2,2'-azobis (2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl)peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethylhexanoate, t-butyl peroxy-2-ethylhexanoate, t-butyl peroxyacetate, di-t-amyl peroxyacetate, t-butyl peroxide, di t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3.3-di-(t-butylperoxy)-butyrate, t-amyl perbenzoate, t-butyl perbenzoate and ethyl 3,3-di-(t-amylperoxy)-butyrate.

In certain embodiments of the methods, the emulsifier is a member selected from the group consisting of palmitamidopropyltrimonium chloride, distearyl diimonium chloride, cetyltrimethylammonium chloride, quaternary ammonium compounds, fatty amines, aliphatic ammonium halides, alkyldimethyl benzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethylaminoethyl methacrylate), poly(acrylamide-co-diallyldimethylammonium chloride), poly(allylamine), polybis(2-chloroethyl)ether-alt-1,3-bis(3-(dimethylamino)propylurea quaternized, poly(dimethylamine-co-epichlorohydrin-co-ethylenediamine), polyalkylene glycol ether, polyvinyl acetate, copolymers of polyvinyl acetate, polyacrylamide, poly(N-isopropylacrylamide), poly (2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene), polyvinyl pyrrolidone, copolymers of polyvinyl pyrrolidone, 1H-Imidazolium, 1-ethenyl-3-methyl-, chloride, polymer with 1-ethenyl-2-pyrrolidinone, vinyl acetate and gum arabic.

BRIEF DESCRIPTION OF SEVERAL VIEWS OF THE DRAWINGS

The invention will be described in conjunction with the following drawings, wherein:

FIGS. 4A and 4B show SEMs of fabric at 570× and 1950× magnification, wherein Example 4 capsules have been tested using the Detergent Dissolution Test method. Notice that fully intact capsules with a friable membrane surrounding an interior core are observed.

FIGS. 5A and 5B show SEMs of fabric at 710× and 1550× magnification, wherein Example 5 capsules have been tested using the Detergent Dissolution Test method. Notice that fully intact capsules with a friable membrane surrounding an interior core are observed.

DETAILED DESCRIPTION OF PREFERRED EMBODIMENTS OF THE INVENTION

Glossary

Figure 1:
FIG. 1 shows Scanning Electron Micrographs (SEMs) of a fabric wherein Example 1 capsules have been tested using the Detergent Dissolution Test Method. Notice that no intact capsules are observed.
Figure 2A:
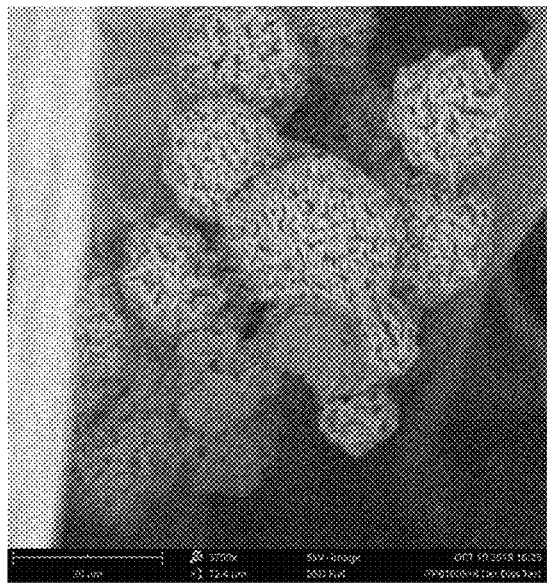
FIGS. 2A and 2B show SEMs of fabric at 3700× and 4500× magnification, wherein Example 2 capsules have been tested using the Detergent Dissolution Test method. Notice that gelled acrylate polymer containing perfume is observed. No membrane is observed surrounding the gelled polymer.
Figure 2B:
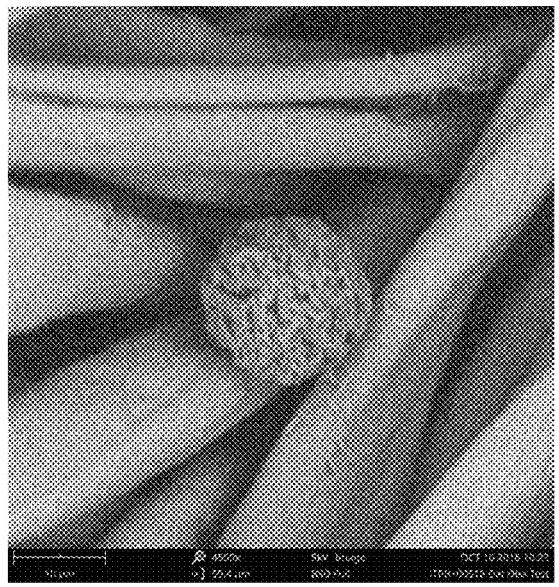

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell" and "wall" are synonyms, which refer to barriers at least partially surrounding the core of the particles of the invention.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Advantages of the Invention

One or more of the following benefits are provided by preferred embodiments of the invention.

The inventive particles adhere onto desired substrates via the use of viscoelastic and electrostatic interactions. By adhering large particles as well as small particles during the rinse off application, greater volumes of active material can be delivered with a higher delivery efficiency of the encapsulated active. Conventional capsules are limited to the deposition of small particles, which carry much less volume of active material. Only a fraction of these small microcapsules fracture during use, resulting in significantly lower delivery efficiency of the encapsulated active.

The inventors have discovered that by adjusting the composition of the shell material of the particles, one can control the nature of the core material in the final product (liquid pool of material to a sponge of semisolid material), without the use of high melting waxes or high melting polymers.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active.

Particles

The invention addresses one or more of the prior art deficiencies described above by providing controlled release particles. The particles are particularly well-suited for use in encapsulation of hydrophobic, nonpolar materials. The controlled release particles are preferably anhydrous and sufficiently friable to release the hydrophobic active ingredient in response to friction.

Figure 3A:
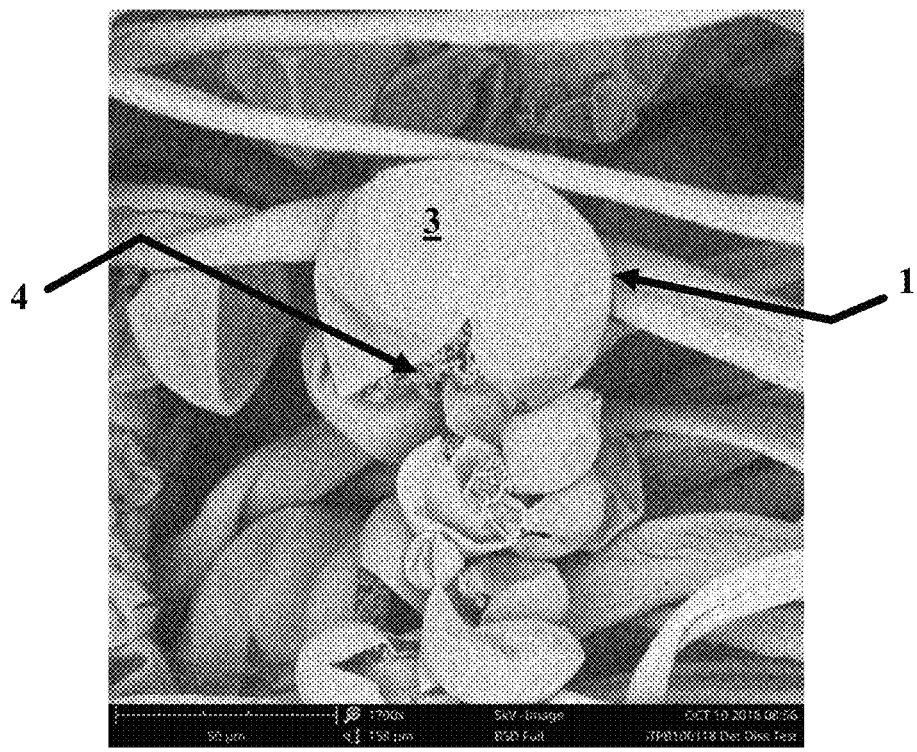
FIGS. 3A and 3B show SEMs at 1700× and 960× magnification of capsule embodiments of the invention on fabrics.
Figure 3B:
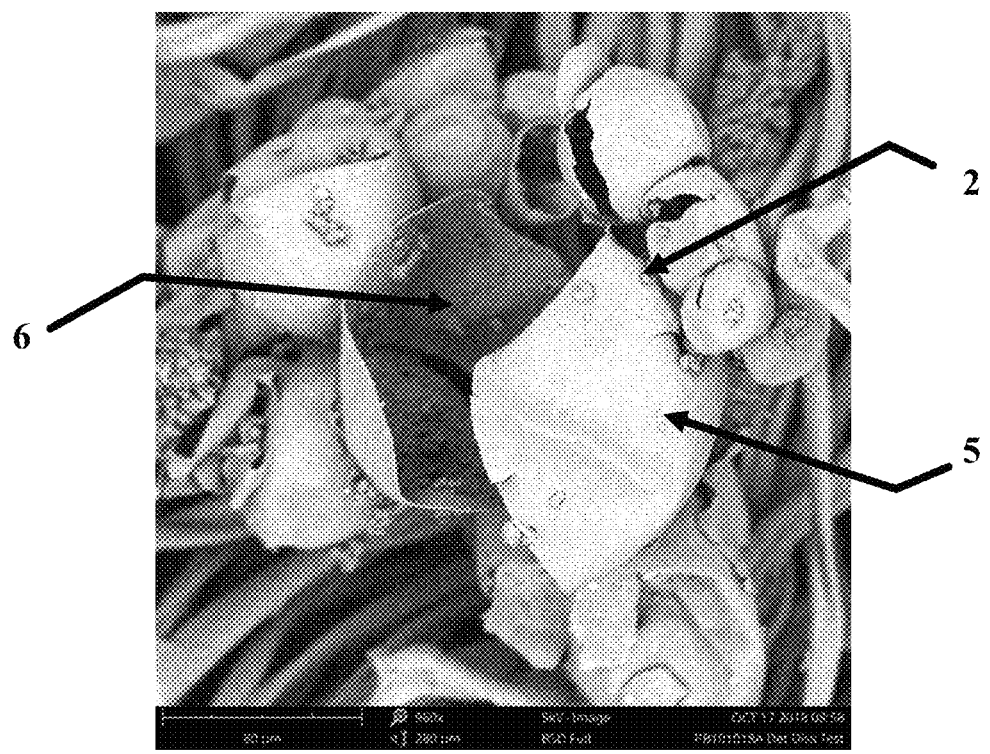
Figure 6A:
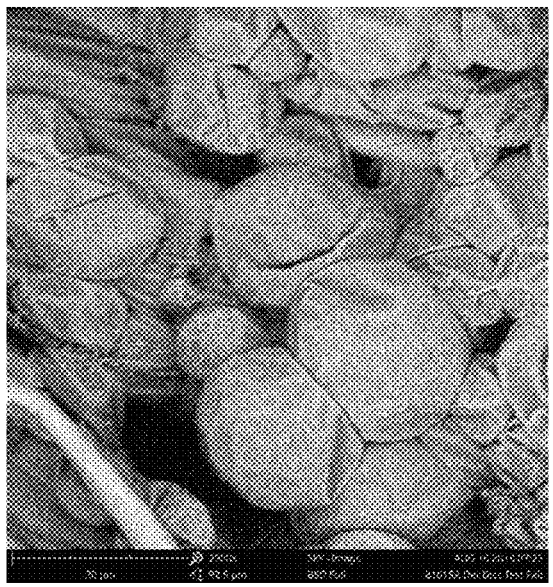
FIGS. 6A and 6B show SEMs of fabric at 2900× and 2000× magnification, wherein Example 6 capsules have been tested using the Detergent Dissolution Test method. Notice that fully intact capsules with a friable membrane surrounding an interior core are observed.
Figure 6B:
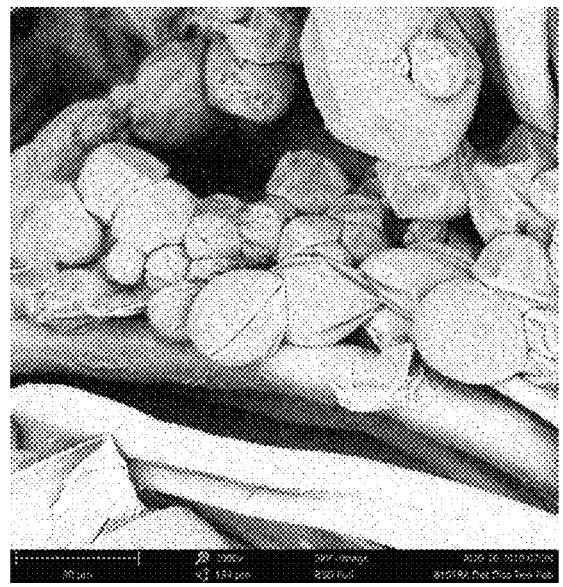
Figure 7A:
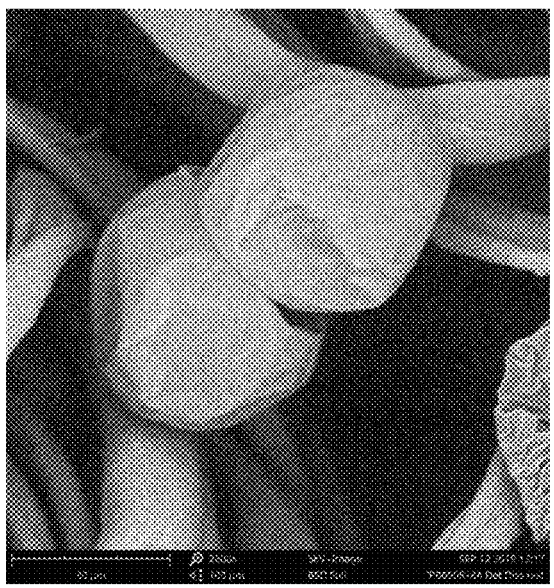
FIGS. 7A and 7B show SEMs of fabric at 2600× and 3800× magnification, wherein Example 7 capsules have been tested using the Detergent Dissolution Test method. Notice that fully intact capsules with a friable membrane surrounding an interior core are observed
Figure 7B:
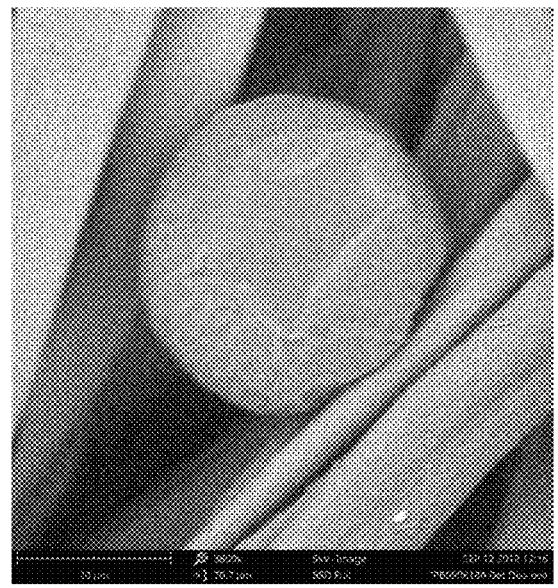
Figure 8A:
FIGS. 8A and 8B show SEMs of fabric at 2350× and 620× magnification, wherein Example 8 capsules have been tested using the Detergent Dissolution Test method. Notice that fully intact, capsules with a uniquely deformable membrane surrounding an interior core are observed.
Figure 8B:
Figure 9A:
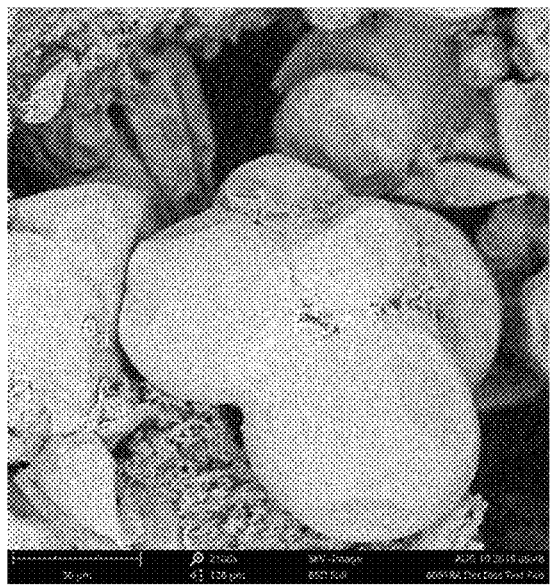
FIGS. 9A and 9B show SEMs of fabric at 2100× and 670× magnification, wherein Example 9 capsules have been tested using the Detergent Dissolution Test method. Notice that fully intact, capsules with a friable membrane, with a low level of deformation, and adhesion between capsules is observed.
Figure 9B:
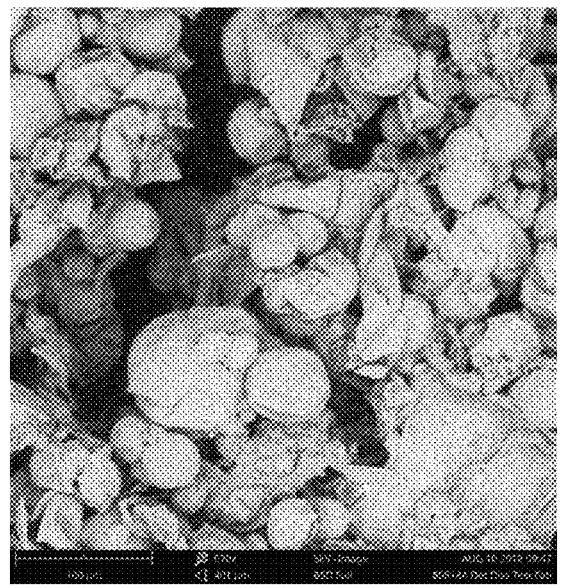

Referring to FIG. 3A, capsule (or particle) 1 comprises semisolid, spongelike core 4 that reduces the diffusion rate of the least one hydrophobic active ingredient and wall (or shell) 3 at least partially surrounding core 4. In FIG. 3B, the capsule (or particle) 2 comprises a non-semisolid core 6 (pool of liquid that has been released from the core of the capsule immediately upon fracture of the capsule) comprising at least one hydrophobic active ingredient and wall (or shell) 5. The wall (or shell) comprises a friable membrane. The core can be manipulated from a semi-solid, spongelike material to a low viscosity liquid depending on the chemistry employed.

The particles are preferably used in a consumer product composition, such as, e.g., a cleaning composition, a fabric care composition and/or a personal care composition.

The acrylate copolymer preferably comprises a member selected from the group consisting of a urethane acrylate oligomer bearing both acrylate and isocyanate functionalities, wherein the isocyanate content in the oligomer ranges from about 5 wt. % to about 15 wt. %, wherein the acrylate content in the oligomer can be from about 20 wt. % to about 50 wt. %. The acrylate copolymer preferably comprises Sartomer CN9302.

Optionally, the copolymer of polyacrylamide and polyacrylate preferably comprises a reaction product of two or more materials comprising 1) a water-soluble monomer containing at least one vinyl group, preferably an ethylenically unsaturated carboxylic acid amide of a polyamine, and 2) a water dispersible acrylate comprising ethylenically unsaturated monomers manifesting poor to moderately hydrophilic properties, having a water solubility less than 5 grams per liter at 25° C. Suitable water-soluble vinyl monomers include, for example, N,N'-methylene-bis-acrylamide, N,N'-methylene-bis-methacrylamide, and other lower alkylidene-bis-acrylamides. Suitable water dispersible acrylates include, for example, ethylene glycol dimethacrylate, neopentyl glycol diacrylate, ethoxylated (4) bisphenol A diacrylate and pentaerythritol tetraacrylate.

The polyurea preferably comprises a reaction product of 1) an isocyanate functionality and 2) an amine functionality. Preferably, the isocyanate functionality is provided by polymeric isocyanates with a molecular weight greater than 300 grams per mole. Preferably, the amine functionality is provided by, for example, acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, pentaethylene hexamine, hexamethylenetetramine, tetraethylene pentamine, and Girard's reagent; silicone amines such as aminopropylsilsequioxane oligomer, water borne amino alkyl silsequioxane oligomers, trihydroxysilylpropylamine condensate, 3-aminopropyl(diethoxy)methylsilane, [3-(2-aminoethyl)-aminopropyl] methyl-dimethoxysilane, [3-(2-aminoethyl)-aminopropyl]trimethoxysilane.

The quaternary amine is preferably a material that has a primary amine moiety and a quaternary amine moiety. The primary amine moiety can preferably react with isocyanate functionality to form a polyurea layer, and the highly polar quaternary amine functionality interacts with the surrounding aqueous phase. Suitable quaternary amine materials include, for example, Girard's reagent. Other suitable quaternary amines include but are not limited to compounds represented by formulas (1)-(4) below.

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 47 wt. % or 59 wt. % or 66 wt. % to 73 wt. % or 78 wt. % or 81 wt. % or 93.5 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, *eucalyptus*, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Suitable moldicides further include but are not limited to fungicidal compounds such as, e.g., isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethyl-isothiazolinone, 4,5-Dichloro-2-n-octyl-3 (2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point.

Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying agents include unsaturated natural resins such as rosin or derivatives thereof, such as rosin esters of polyols such as glycerol or pentaerythritol, hydrogenerated rosins or dehydrogenerated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

The emulsifier is present in the suspension, on a dry basis (weight of emulsifier per weight of dry matter in the suspension), of the invention in an amount effective to achieve the desired particle size distribution. The amount can be, e.g., from about 1.5 wt. % to about 10 wt. % or at least 1.5 wt. %, or at least 5 wt. % or at least 7.4 wt. % or at least 8.2 wt. %, or at least 10 wt. % or not greater than 10 wt. %.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17. Of course, emulsifiers/surfactants of lower and higher HLB values that achieve the same objective as noted are also included.

Exemplary emulsifiers include, but are not limited to gums such as acacia gum, gum arabic, konjac gum, and xantham gum; poly(meth)acrylic acids and derivatives; and poly(styrene-co-maleic acid) and derivatives and the like. Most preferably, the emulsifier/emulsion stabilizer is a polyvinyl pyrrolidone, copolymers of polyvinyl pyrrolidone with vinyl acetate, vinyl alcohol, vinyl imidazole; polyglycerol oleates.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof, alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelalkenyl succinic anhydride condensation products; alkyl ester sulfates; naphthalene sulfonates; naphthalene formaldehyde condensates; alkyl sulfonamides; sufonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesuifonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy-modified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, 1H-Imidazolium, 1-ethenyl-3-methyl-, chloride, polymer with 1-ethenyl-2-pyrrolidinone, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable cationic acrylates include, but are not limited to [2-(Acryloyloxy)ethyl]trimethylammonium methyl sulfate solution, 80% in water (Signa catalong #408115), [2-(Methacryloyloxy)ethyl]trimethylammonium methyl sulfate solution, 80% in water (Sigma Cat #408123), [3-(Methacryloylamino)propyl]trimethylammonium chloride solution, 50% in water (Sigma Cat #280658), (3-Acrylamidopropyl)trimethylammonium chloride solution, 75% in water (Sigma Cat #448281), [2-(Acryloyloxy)ethyl]trimethylammonium chloride solution (Sigma Cat #496146).

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; sorbitol ester alkoxylates; ethoxylated castor oil; amides of fatty acids such as stearamide, lauramide diethanolamide, and lauramide monoethanolamide; aryl ethers of polyoxyalkylene glycols such as polyoxyethylene glycol nonylphenyl ether and polypropylene glycol stearyl ether. Also preferred as non-ionic emulsifiers are various latex materials, stearates, lecithins, In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates, urethane acrylates comprising isocyanate and acrylate functionalities.

In certain embodiments, the oil soluble acid monomer or oligomer comprises acid acrylates, containing more than one carboxylic acid group.

In certain embodiments, the water soluble acid comprises acids that have more than one carboxylic acid group.

The amine comprises linear aliphatic amines, aromatic amines, silicone amines, branched amines, polyamines, and amino acids. Generally, amines are listed by their pKa values, and this defines whether the amine is acidic, basic, or neutral. Acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, guanidine carbonate. pentaethylene hexamine, hexamethylenetetramine, tetraethylene pentamine, and Girard's reagent; silicone amines such as aminopropylsilsequioxane oligomer, water borne amino alkyl silsequioxane oligomers, trihydroxysilyl-propylamine condensate, 3-aminopropyl(diethoxy)methylsilane, [3-(2-aminoethyl)-aminopropyl]methyldimethoxysilae, [3-(2-aminoethyl)-aminopropyl]trimethoxysilane; guanidine carbonate; amino acids such as Aspartic acid, glutamic acid, lysine, arginine, histidine, glycine, alanine, serine, threonine, tyrosine, asparagine, glutamione, cysteine.

In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates. Exemplary isocyanates are selected from the group consisting of hexamethylene diisocyanates (Desmodur N3600, Desmodur N3800, Desmodur N3900, Desmodur N3200, Desmodur N3400, Takenate D-170N), isophorone diisocyanates (Desmodur XP2565, Desmodur Z4470), blends of hexamethylene diisocyanate and isophorone diisocyanate (Desmodur XP2847, Desmodur XP2489, Desmodur XP2838, Desmodur XP2763), pentane-1,5-diisocyanate (Stabio D-370N, Stabio D-376N), xylylene diisocyanate (Takenate 500, Takenate 600, Takenate D-110N, Takenate D-131N), polymeric methylene diphenyl diisocyanate (Mondur MR Lite), polymeric MDI (Desmodur VK 5, Desmodur VL RIO, Desmodur 44V40L, Desmodur 44V70L), polyether modified hydrophilic polyisocyanates (Bayhydur XP2451/1, Bayhydur XP2547, Bayhydur XP2759, Bayhydur Ultra 304, Bayhydur Ultra 2487/1), CN9302, ionically modified isocyanates (Bayhydur 2858 XP, Bayhydur XP2759, Bayhydur eco 7190), and the like.

In certain embodiments the oil soluble acid monomer or oligomer comprises acid acrylates containing more than one carboxylic acid group. Exemplary oil soluble acid monomers or oligomers are selected from the group consisting of carboxylic acid and anhydride containing methacrylate oligomer, ethoxylated trimethylolpropane triacrylate monomer, carboxylic acid containing acrylate oligomer tripropylene glycol diacrylate monomer. Examples of commercially available resins are Sarbox SB500E50, Sabrox SB520E35

In certain embodiments, the water soluble acid comprises acids that have more than one carboxylic acid group. Exemplary water soluble acids are selected from the group consisting of alkyl-based diacids such as malonic, succinic, adipic, fumaric, maleic, sebacic and tartaric. Diacids such as succinic, adipic or malonic acid are also preferred. A triacid such as citric acid, for example, is usable. Polyacids that comprise segments of poly(alpha-hydroxy acids, polyesters of glycolic acid, DL lactic acid, L lactic acid, oligomers, monomers or combinations thereof, polymers containing one or more groups such as anhydride, a orthoester and/or a phosphoester, are also usable.

The amine is present in particles of the invention in an amount effective to crosslink the isocyanate moiety on the oligomer to an extent effective to provide the particles with desired durability. The amount of amine on a dry basis (weight of amine per weight of dry matter in the suspension) can be, e.g., from 0.1 wt. % or 0.6 wt. % or 0.9 wt. % or 1.3 wt. % to 1.8 wt. % or 2.3 wt. % or 3.3 wt. %.

In certain embodiments, the acrylamide comprises a member selected from the group consisting of water soluble terpolymers. The water-soluble terpolymer of this invention consists essentially of a water-soluble monomer containing at least one vinyl groups, preferably an ethylenically unsaturated carboxylic acid amide of a polyamine. Suitable water-soluble vinyl monomers include, for example, N,N'-methylene-bis-acrylamide, N,N'-methylene-bis-methacrylamide, other lower alkylidene-bis-acrylamides where the alkylidene group has up to four carbon atoms, ethylene glycol diacrylate, ethylene glycol dimethacrylate, and propylene glycol dimethacrylate. N,N'-methylene-bis-acrylamide is most preferred. Higher amounts of polyvinyl monomer can lead to partial or complete water insolubility of the terpolymers.

The amount of acrylamide on a dry basis (weight of acrylamide per weight of dry matter in the suspension) can be, e.g., about 0.2 wt. % to about 6.8 wt. %, or at least 0.2 wt. %, or at least 1.3 wt. %, or at least 1.8 wt. %, or at least 2.6 wt. %, or at least 3.7 wt. %, or at least 4.8 wt. %, or at least 6.8 wt. %, or not more than 6.8 wt. % of the particles.

The acrylate material is preferably a member selected from the group consisting of ethylenically unsaturated monomers manifesting poor to moderately hydrophilic properties, include by way of illustration and not limitation, allyl meth acrylate, triethylene glycol dimethacrylate, ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates, tetraethylene glycol dimethacrylate, polyethylene glycol dimethacrylate, 1,3-butylene glycol diacrylate, 1,4-butanediol dimethacrylate, 1,4-butaneidiol diacrylate, diethylene glycol diacrylate, 1,6-hexanediol diacrylate, 1,6-hexanediol dimethacrylate, neo pentylglycol diacrylate, polyethylene glycol diacrylate, tetraethylene glycol diacrylate, triethylene glycol diacrylate, 1,3-butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpro panetriacrylate, pentaerythritol triacrylate, ethoxylated trim ethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate. The desired water dispersible acrylate is insufficiently hydrophilic such that it will not form a gel as it oligomerizes in the water phase and, preferably, is sufficiently hydrophobic, but not so hydrophobic, such that oligomers thereof will tend to migrate to the water/oil phase interface rather than form discrete particles or beads of the polymerized polymer in the water phase. Generally, a poor to moderately hydrophilic monomer is one that has a solubility of less than about 40 grams per liter (g/L), or even less than 30 g/L, or preferably from about 0.1 g/L to about 40 g/L, or even from about 0.1 g/L to 25 g/L, or even from about 5 g/L to 30 g/L, or even from about 10 to 25 g/L as measured in deionized water at 20° C.

The amount of acrylate material on a dry basis (weight of water dispersible acrylate per weight of dry matter in the suspension) can be, e.g., from about 0.6 wt. % to about 18.8 wt. %, or at least 0.6 wt. %, or at least 3.6 wt. % or at least 5.0 wt. % or at least 7.3 wt. % or at least 10.3 wt. % or at least 13.3 wt. %, or at least 18.8 wt. %, or no more than 18.8 wt. % of the particles.

The water phase compositions and the hydrophobic oil phase compositions may further contain other ingredients conventional in the art including, e.g., chain transfer agents and/or agents which help control the molecular weight/degree of polymerization of the wall forming monomer, thereby aiding in the movement of the oligomer through the respective oil phase and water phase compositions. Suitable chain transfer agents include, but are not limited to, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercaptoproprionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present, the chain transfer agents are preferably used in amounts ranging from 0.01 to 5%, preferably from 0.5 to 3%, by weight with respect to the monomers and/or oligomers employed.

Preferred free radical initiators include peroxy initiators, azo initiators, peroxides, and compounds such as 2,2'-azobismethylbutyronitrile and dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis (2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl) peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3.3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably, the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps of wall formation and hardening or polymerizing of the capsule wall material. The amount of initiator (weight of initiator divided by the weight of dry matter in the suspension) can be, e.g., from about 0.13 wt. % to about 4.2 wt. %, or at least 0.13 wt. %, or at least 0.8 wt. %, or at least 2.3 wt. %, or at least 3.0 wt. %, or at least 4.2 wt. %, or no more than 4.2 wt. % of the particles.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof, polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, 1H-Imidazolium, 1-ethenyl-3-methyl-, chloride, polymer with 1-ethenyl-2-pyrrolidinone, polyamines, polysaccharides with cationic modification, and mixtures thereof. Polysaccharides can be employed with cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The deposition aid is present in the controlled release particles in an amount on a dry basis (weight of deposition aid per weight of dry matter in the suspension) from 0.5 wt. % or 1 wt. % or 1.5 wt. % or 3.5 wt. % to 5 wt. % or 7 wt. % of the weight of the particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles according to the present teaching are made in a multi-step process as described below. For convenience, the process is presented in the preferred mode which involves one aqueous phase composition and one hydrophobic oil phase composition. Nonetheless, those skilled in the art will readily appreciate that the aqueous phase composition may be prepared as a dual phase composition to which the hydrophobic oil phase composition is added or a three or more components composition where various ingredients are preferably isolated from one another until desired so as to avoid undue or undesired activation of the aqueous phase monomers or oligomers.

The hydrophobic oil phase composition is formed by combining the hydrophobic active core material with oil soluble monomers and oligomers. Most preferably this is conducted under moderate increased temperature so as to facilitate the solubilization or suspension of the monomers, oligomers, and other ingredients that may be present, including nucleating agents, in the core material. This is particularly useful if the core material is a solid or wax or a high viscosity material. Once a stable solution or suspension of the core material is prepared, the hydrophobic oil phase initiator is then added to the combination and the composition mixed to ensure good dispersion of the hydrophobic oil phase initiator. Once again, if the temperature of the mixture had been elevated to aid in getting the hydrophobic oil phase monomer into solution/suspension, then the mixture should be cooled or allowed to cool to a temperature that is safely below the lowest key activation temperature of the one or more hydrophobic oil phase initiators. It is best to cool the resultant oil phase composition before adding it to the aqueous phase composition.

Not to be limited by theory, the reaction of an isocyanate with a carboxylic acid has a reaction product that is a mixed carbamic-carboxylic anhydride. When a polymeric isocyanate is utilized, the formed carbamic-carboxylic anhydride is stable. This moiety can be formed within the hydrophobic active material or at the oil-water interface. Preferably, the reaction is undertaken at room temperature.

The mixture is agitated until the desired droplet size of oil phase composition is attained. In order to establish a wall at the oil-water interface, an amine is added to the aqueous phase followed by pH adjustment. The addition of the amine partitions isocyanate in the hydrophobic oil phase to the interface. The interfacial reaction of the amine with the isocyanate functionality results in a membrane at the oil-water interface that stabilizes the oil droplets. Droplets are preferably from about 10 microns to about 75 microns, and more preferably from about 20 microns to about 50 microns in volume average diameter. Once this membrane is established, no further decrease in particle size of the oil droplets is observed. The reactor contents are agitated for 30 minutes to 5 hours, depending on the emulsifying properties of the hydrophobic oil phase. It is desired to maintain a temperature of the reactor below 40° C., in order to facilitate controlled membrane formation.

Optionally, a mixture of water dispersible acrylate in water and initiator is also added to the reactor vessel. The temperature of the reaction vessel is raised to the activation temperature of the hydrophobic oil phase initiator and aqueous phase initiator. It is desired to use the same initiator in both phases, or alternatively, initiators that have activation temperatures that are within 5° C. of each other. If multiple initiators are incorporated into the hydrophobic oil phase and/or aqueous phase, it is desired to raise the temperature to the activation temperature of the low temperature initiator. Since the dual functional acrylate oligomer (acid acrylate and/or urethane acrylate comprising isocyanate and acrylate functionalities) is already at the oil-water interface, the increase in temperature activates the crosslinking of acrylate moieties to increase the crosslink density of the shell to form a strong polymer composition. Acrylamides and water dispersible acrylates from the aqueous phase will also partition to the interface to increase the crosslink density of the shell. Here, the higher temperature is maintained until the capsules are fully formed, generally from about 1 to 8 hours.

Although not critical to the basic embodiment of the present teaching, the rate of temperature increase in the activation of the initiators can also influence the ultimate performance and characteristics of the resultant microcapsules. In this regard it is preferred that temperature increases be performed over an extended period of time, preferably over a period of 25 to 40 minutes, more preferably about 30 minutes. The rate of increase during that period may vary from about 20° C. per hour to about 40° C. per hour. Of course, these are general ranges and the same may be somewhat lower or somewhat higher depending upon the selected materials and the activation temperatures of the initiators.

In certain embodiments, the suspension of controlled release particles is dehydrated in order to expose the particles to a higher temperature to achieve a higher degree of crosslinking of the monomers.

In certain embodiments of providing a powder composition of the invention, spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

In powder composition embodiments, the silica flow aid is added to the dry powder to improve the flowability of the powder. Addition of the silica flow aid minimizes the agglomeration of particles during the heating, packing, and conveyance processes.

Advantages of at least some embodiments of the inventive method include at least one or at least two or at least three or at least four or all five of the following:
a) One-pot process: membrane developed from oil and aqueous phases in a single process.
b) Flexibility in active: membrane is developed at the oil-water interface via the use of interfacial polymerization.
c) Low permeabeality of the shell.
d) Can be used in a variety of applications, including but not limited to household care, personal care, beauty care, etc.
e) Preferably utilizes a commercially available, relatively inexpensive technique to further engineer the particle.

Compositions Containing the Particles

The invention further comprises compositions comprising the controlled release particles. Such compositions include but are not limited baby care, beauty care, fabric & home care, family care, feminine care, health care, snack and/or beverage products or devices intended to be used or consumed in the form as sold, and not intended for subsequent commercial manufacture or modification. Such products include but are not limited to fine fragrances (e.g., perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 sec$^{-1}$ shear rate and at 21° C., of from 1 to 7000 cps and a low shear viscosity, at 0.5 sec$^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry comprising particles of the invention. Said slurry may be combined with an adjunct ingredient to form a composition, for example, a consumer product. In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose and cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol, non-polar solvents including but not limited to mineral oil, perfume raw materials, silicone oils, hydrocarbon paraffin oils, and mixtures thereof.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition was used for capsule making.

TABLE 1

| Perfume oil composition | |
|---|---|
| Material | wt % |
| Ethyl-2-Methylbutyrate (C7H14O2) | 0.45% |
| Limonene-D | 1.10% |
| Dihydromyrcenol (C10H20O) | 4.31% |
| Tetra hydro Linalool (C10H22O) | 0.54% |
| Benzyl Acetate FCC (C9H10O2) | 3.13% |
| Citronellol (C10H20O) | 0.82% |
| Linalyl Acetate Synthetic (C12H20O2) | 0.11% |
| Undeavertol, C11H22O | 1.21% |
| Methyl Anthranilate (DEA) (C8H9NO2) | 0.27% |
| Gamma-Nonanoic (C9H16O2) | 4.64% |
| Cycalcet (C12H16O2) | 5.72% |
| Floralozone (C13H18O) | 0.60% |
| Yara Yara (beta-napthyl methyl ether) | 5.71% |
| Fruitate (C13H20O2) | 0.11% |
| Cycylamen aldehyde (C13H18O) | 0.29% |
| Methyl Ionone Gamma Coeur (C13H20O) | 0.39% |
| Cycalprop (C13H18O2) | 3.06% |
| Lilial (C14H20O) | 12.98% |
| Hedione C13H22O3 | 5.54% |
| Triethyl citrate (C12H20O7) | 5.57% |
| E Super Iso (C16H26O4) | 14.46% |
| Hexyl Salicylate (C13H18O3) | 5.58% |

TABLE 1-continued

| Perfume oil composition | |
|---|---|
| Material | wt % |
| Hexyl Cinnamic Aldehyde (C18H20O) | 2.24% |
| Galaxolide 50% IPM | 5.81% |
| Benzyl Salicylate (C14H12O3) | 15.36% |

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of liquid detergent added to 99 grams of water, then filtered through Whatman 597 filter catalog number 10311808) is added powder or slurry that achieves a concentration of approximately 1 wt. % perfume oil in the detergent solution. For water solubility, the powder is simply dosed into water rather than detergent solution. For the Detergent Dissolution Test, the sample is mixed at 200 RPM for 30 minutes at 33.3° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are two techniques utilized to evaluate odor of fabrics:

1) The dried fabrics from the Detergent Dissolution Test+Fabric Preparation test are evaluated olfactively by a panel before and after rubbing. A subjective grading scale is used to grade fabrics before rubbing and after rubbing. In the case of before rubbing, the control that is used is a fabric treated with neat fragrance oil in the detergent solution. In the case of rubbed fabric, the control is the fabric before rubbing is performed.

TABLE 2

| Odor grading scale | |
|---|---|
| Odor Grade | Description |
| 0 | No Difference vs. Control |
| 1 | Slight Difference vs. Control |
| 2 | Noticeable Difference vs. Control (detectable difference) |
| 3 | Obvious difference vs. control (high intensity vs. control) |
| 4 | Very High Intensity vs. control |

The dried fabrics from the Detergent Dissolution Test+Fabric Preparation test are evaluated by an Odor Meter (Shinyei Technology model OMX-SRM) before and after rubbing. This method reports the total concentration of volatiles in the headspace and is reported in milligrams per cubic meter as a function of time Free Oil Approximately 0.20 grams to 0.27 grams of microcapsule slurry is preweighed in a 20 mL glass scintillation vial. 10 mL of hexane is added to the slurry. The scintillation vial is overturned 10 times to allow for mixing. The scintillation vial is then placed on a platform shaker that shakes the vial at a frequency of 1/sec to allow for mixing of the contents, for 10 minutes. The scintillation vial is allowed to sit unagitated at room temperature for 10 minutes. Sodium sulfate or sodium chloride could be added if there is a lack of phase separation of the hexane layer observed. Approximately 3 mL of the clear hexane layer is removed, placed into a syringe filter (0.45 micron, 25 mm diameter Acrodisc PTFE filter), and decanted into a GC vial. The sample is analyzed by Gas Chromatography. GC conditions are shown in Table 3 below.

TABLE 3

| GC CONDITIONS |
| --- |
| Oven |
| Initial Temperature: 40° C.<br>Rate: 5° C./min to 250° C.<br>Hold Time at Inlet Temp: 2 minutes<br>Run Time: 44.00 minutes |
| Inlet |
| Mode: Split<br>Split Ratio: 8:1<br>Initial Temperature: 240° C.<br>Column Flow: 1.2 mL/min (constant flow mode)<br>Column Type: DB-5, 30 m, 0.25 mm duameter,<br>0.25 μm film thickness<br>Basic MSD Settings |
| Low Mass: 50<br>High Mass: 550<br>Threshold: 500<br>MS Quad Temperature: 150° C.<br>MS Source Temperature: 230° C.<br>Transfer Line Temperature: 250° C. |

Biodegradability

Biodegradability testing is carried out according to protocol OECD 301D. 5 mg/L material is placed into Biochemical Oxygen Demand (BOD) bottles in water collected from the Lehigh River (Bethlehem, PA). The samples consist of a negative control (a material that is not biodegradable), a positive control (polysaccharide that is known to be fully biodegradable), test samples of unknown degradability, and when possible, a sample that simply combines the raw materials used to make the microcapsules, but not crosslinked. The bottles are checked for dissolved oxygen at 0, 7, 14, and 21 days. Intermittent points can also be taken since an asymptotic value may be reached much sooner than 21 days. The percent degradation is analyzed against the positive control starch. See Example 12 for a detailed description of the analysis and calculations of Biodegradability Index Example 1. STPB100118 Comparative Capsule 1: Isocyanate/Amine Capsules with No Acid Acrylate 53 g perfume is mixed with 5 g diisophorone diisocyanate and stirred at room temperature for 5 minutes using a magnetic stir bar to achieve a homogeneous solution. The prepared oil phase is added to 210 g of a 5 wt % PVP-K90 aqueous phase while agitating the aqueous phase using a Caframo BDC6015, 4-blade pitched agitator shaft 1" diameter, at 750 rpm for 25 minutes to form a premix emulsion. Approximately 4 grams of a 20 wt % solution of guanidine carbonate is added to the emulsion. The contents are allowed to react for 5 hours at room temperature, followed by 4 hours at 50° C. No capsules are formed, only pools of oil are observed.

Example 2. Comparative Capsule 2: Isocyanate/Acid Acrylate Capsules with No Amine Reaction at Oil/Water Interface (STPB100518)

60 g perfume oil is mixed with 1.18 g CN9302, 2.36 g Sarbox SE50, 5.1 g Mondur MR Light, and 0.34 grams Vazo-52, using a magnetic stirrer, at room temperature, to make a homogeneous solution. The mixture is added to 210 grams of 5 wt % PVP K-90 solution while agitating the aqueous phase using a Caframo BDC6015, 4-blade pitched agitator shaft 1" diameter, at 750 rpm for 25 minutes to form a premix emulsion. Water borne silsesquioxane oligomer WSA9911 (2 g) is added dropwise and the reaction mixture is allowed to stir for next 5 hr at room temperature. The contents are allowed to react for 5 hours at room temperature, followed by 4 hours at 60° C. Microcapsules were observed, but the capsules look like a sponge of material. There is no hard layer of material observed around the spongy capsules.

Example 3. Comparative Capsule 3: Acid Acrylate in Core with Initiators, Acrylamide, Etc. But No Isocyanate or Amine 60 g perfume oil is mixed with 1.18 g CN9302, 2.36 g Sarbox SE50, and 0.34 grams Vazo-52, using a magnetic stirrer, at room temperature, to make a homogeneous solution. The mixture is added to 210 grams of 5 wt % PVP K-90 solution while agitating the aqueous phase using a Caframo BDC6015, 4-blade pitched agitator shaft 1" diameter, at 750 rpm for 25 minutes to form a premix emulsion. Water borne silsesquioxane oligomer WSA9911 (2 g) is added dropwise and the reaction mixture is allowed to stir for next 5 hr at room temperature. 0.35 g of Vazo-52 is added to the solution and contents were allowed to heat gradually to 60° C. for 4 hours, followed by overnight stirring while cooling of the batch. No microcapsules were observed.

Example 4: STPB081318A

Prepare Oil Phase: mix 53 g of Perfume oil, 1.1 g of CN9302, 2.21 g of Sarbox SE50, 0.8 g of N,N'-Methylenebis (acrylamide), 6.3 g of Mondur MR—Light and 0.34 g of Vazo-52 respectively. Contents of the mixture are allowed to stir at room temperature using a magnetic stir bar at 100-150 rpm for 20 minutes.

Prepare Aqueous Phase: 210 grams of 5 wt. % aqueous solution of Sokalan K90P is prepared Emulsion Formation: The prepared oil phase is added into the aqueous phase while agitating the aqueous phase using a Caframo BDC6015, 4-blade pitched agitator shaft 1" diameter, at 750 rpm for 25 minutes to form a premix emulsion. An aliquot is analyzed by optical microscopy to understand particle size of the emulsion. Water borne silsesquioxane oligomer WSA9911 (2 g) is added dropwise and the reaction mixture is allowed to stir for next 5 hr at room temperature. 0.35 g of Vazo-52 and 1 g of N,N'-Methylenebis(acrylamide) are added to the solution and contents are allowed to heat gradually to 76° C. for 4 hours, followed by overnight stirring while cooling the batch.

Observations: Optical microscopy suggest that there is no free-flowing fragrance in the aqueous emulsion after the encapsulation process. There was no need for pH adjustment.

Example 5: STPB081718A

The procedure of Example 4 (STPB081318A) is followed, with the following modification.

Once premix emulsion is formed, water borne amino alkyl silsesquioxane oligomer WSA7011 (2 g) was added dropwise and the mixture is treated as per described in Example (STPB081318A)

Example 6: STPB081018A

The procedure detailed in Example 8 (STPB080118B) is followed, with the following modification.

Once premix of emulsion is formed, water borne amino alkyl silsesquioxane oligomer WSA7011 (1.2 g) was added dropwise and the mixture is treated as per described in Example 8 (STPB080118B)

Example 7: STPB090618A

Preparation of Oil Phase: 53 g of perfume oil is mixed with 1.0 g of CN9302, 2.5 g of Sarbox E50, 0.8 g of N, N'-Methylenbis(acrylamide), 7.25 g of Mondur MR light and 0.3 g of Vazo-52 are added respectively.

Preparation of Aqueous Phase: 210 grams of 5 wt. % aqueous solution of Sokalan K90P is prepared Emulsion Formation: Prepared oil phase is added as a stream to a stirring aqueous phase using a 4-blade propeller, stirring at 750 rpm. Blend is allowed to mix for 25 minutes and is analyzed under optical microscopy for emulsion formation with desired particle size prior to addition of pre-mixture of WSA-7011 (2 g)+Pentaethylene hexamine (0.5 g). pH stabilization is not necessary. Contents are allowed to stir 5 hours at room temperature followed by 4 hours at 60° C. Later, reaction mixture is let to stir while cooling the batch.

Observation: Morphology of microcapsule is not exactly spherical and delivered superior after rub performance from detergent dissolution test.

Example 8: STPB080118B

Oil Phase is prepared by mixing 53 g of perfume with 3 g of dual functional acrylate and isocyanate specialty resin CN9302, 2 g of Sarbox SE50, 0.8 g of N, N'-Methylenbis (acrylamide), 1.6 g of Mondur MR light, 0.3 g of Vazo-67 are added respectively.

Prepare Aqueous Phase: 210 grams of 5 wt. % aqueous solution of Sokalan K90P is prepared Emulsion Formation: Prepared oil phase is added as a stream to a stirring aqueous phase with a 4-blade propeller, stirring at 750 rpm. Contents were allowed to mix for 25 minutes and were analyzed under optical microscopy for formation of emulsion with desired particle size. 1.5 g of Girad's reagent is added to the mixture as solid and pH of the solution is adjusted between 8.5-9 with aqueous 10% sodium hydroxide solution. Mixture is allowed to stir at room temperature for 5 hours. Later a fresh portion of 0.8 g of N, N'-Methylenebis(acrylamide) and 0.35 g of Vazo-67 are added as solid and reaction mixture is set to heat at 76° C. for 4 hours followed by overnight stirring while cooling the batch.

Example 9: STPB080618A

Preparation of Oil Phase: 53 g of perfume oil is mixed with 3 g of CN9302, 0.5 g of Sarbox E50, 2 g of Ethyleneglycol dimethacrylate, 0.9 g of N, N'-Methylenebis(acrylamide), 4 g of Mondor MR light, 0.3 g of Vazo-67 and 0.3 g of polyfunctional aziridine respectively.

Preparation of Aqueous Phase: 210 grams of 5 wt. % aqueous solution of Sokalan K90P is prepared Emulsion Formation: Prepared oil phase is added as a stream to a stirring aqueous phase with a 4-blade propeller, stirring at 750 rpm. Contents are allowed to mix for 25 minutes and are analyzed under optical microscopy for emulsion formation with desired particle size. 1.5 g of Silicone amine is added dropwise followed by pH stabilization between 8.5-9 using 10% aqueous sodium hydroxide solution. The solution is allowed to stir at aforementioned speed for next 5 hours at room temperature. Later, 0.8 g of N, N'-Methylenebis(acrylamide) and 0.35 g of Vazo-67 are added and mixture is set to heat at 76° C. for 4 hours. Once set temperature is attained, one hour later, 1 g of Ethyleneglycol dimethacrylate is added dropwise, followed by overnight stirring while cooling of the batch.

Observation: Optical microscopy of formed emulsion suggested that polyfunctional aziridine reacts with acidic groups present in Sarbox E50 and further aggregates them. This leads to ultimate discard or escape of the encapsulated perfume.

Example 10. Leakage Stability and Performance Testing

Microcapsules slurries are formulated into liquid detergent (Purex free & clear), to deliver approximately 1.5 wt % fragrance oil in the liquid suspension. The mixtures are aged for 3 weeks at room temperature. After ageing, several tests are performed to evaluate the behavior of the capsules 1) Optical microscopy to observe capsule deflation
2) Approximately 3 grams of the detergent mixture is diluted with 10 grams of water to yield a dilute detergent solution containing approximately 0.35 wt % fragrance oil. This diluted suspension is mixed for 30 minutes at a temperature of 33C at 250 RPM using a magnetic stirrer. Next, approximately 2 mL of the mixed solution is filtered through a black fabric, and allowed to dry overnight. The fabric odor intensity before rubbing and after rubbing is noted.
3) Laundry performance testing is performed with select samples. Approximately 2.5 kg of fabrics are loaded into a Huebsch 2 front load washing machine consisting of 5 bath towels, 3 hand towels, one 100% cotton t-shirt, and one polycotton T-shirt. Liquid detergent is added into a separate compartment, and the microcapsule slurry suspension is added into a separate compartment. Both of these materials are introduced into the wash. No fabric softener or bleach is used. A cold wash is done (approximately 26 minute cycle time shown below). The fabrics are then dried in a Maytag commercial machine dryer on hot cotton cycle for 24 minutes.

TABLE 4

| Laundry cycle description | |
|---|---|
| Time Elapsed (min) | Cycle Description |
| 10 | Wash cycle ends |
| 4 | 1st Rinse Cycle |
| 3 | Spin Cycle |
| 4 | 2nd Rinse Cycle |
| 8 | Spin Cycle |
| 1 | slow spin, end of cycles |

Fabrics are graded before rub and after rub. The results of such testing is shown in the table below. The presence and composition of Mondor ML is critical to assure the formation of an outer layer comprising a reaction product of an amine and an isocyanate and the formation of an intermediate layer under the outer layer and comprising a reaction product of an acid and an isocyanate. When the material is used at low levels, intact capsules that provide strong odor performance from fresh product is observed; however, upon aging the microcapsules in a finished product, leakage of the core material is observed resulting in deflation of the capsule, and loss of odor performance. At sufficient levels, the capsules show strong performance on fabrics from fresh products, show low leakage of the encapsulated core material, and show strong performance in full scale laundry testing.

TABLE 5

Microcapsule slurry leakage stability and fabric odor performance

| | Material | | | | | |
|---|---|---|---|---|---|---|
| | A | B | C | D | E | F |
| Purex Free & Clear | 386.97 | 37.0 | 36.60 | 36.90 | 36.65 | 36.67 |
| Example 4 STPB081318A | 3.0 | | | | | |
| Example 5 STPB081718A | | 3.0 | | | | |
| Example 6 STPB081018A | | | 2.89 | | | |
| Example 7 STPB090618A | | | | 3.02 | | |
| Example 8 STPB080118B | | | | | 3.0 | |
| Example 9 STPB080618A | | | | | | 2.9 |
| Optical Microscopy 3 week aging at RT | Intact capsules. Few fractured. | Intact capsules observed, about 20% fractured | Broken, deflated capsules | Intact capsules | Capsules show high level of deflation | Intact capsules, low deflation |
| Before Rub Fabric Odor (Detergent Dissolution Test) | 2 Noticeable fragrance odor | 2 Noticeable fragrance odor | 0 Low odor | 2 Noticeable fragrance odor | 0 Low Odor | 2.5 Noticeable fragrance odor |
| After Rub Fabric Odor (detergent dissolution test) | 3.5 Significant increase in fabric odor | 3.5 Significant increase in fabric odor | 1 Low odor | 3.5 Significant increase in fabric odor | 1 Low odor | 4 Very strong odor |
| Before Rub Fabric Odor (Laundry test) Fresh Product | 2.5 Noticeable fragrance odor | 2 Noticeable fragrance odor | 0 Low to no odor | 2.5 Noticeable fragrance odor | 2 Noticeable odor | 2.5 Noticeable odor |
| After Rub Fabric Odor (Laundry Test) Fresh Product | 4.0 Very strong odor | 3.5 Strong, noticeable odor | 1.5 Weak odor | 4.0 Very strong odor | 1 No significant increase after rub | 2.5 No significant increase after rub |

Example 11. Extractable Oil Analysis of Microcapsule Slurries

Free oil analysis is completed on the microcapsule slurries. Notice that even after subjecting the microcapsules to a 1 wt % laundry detergent solution for 30 minutes, followed by hexane extraction, the quantity of fragrance oil leaked out of the microcapsules is much less than 500 in most cases. This suggests that the fragrance oil is encapsulated well, and there is very little to no diffusion of the encapsulated oil out of the microcapsule, even though there is clearly a driving force for fragrance leakage out of the microcapsule into a surfactant micellar network.

TABLE 6

Extractable (or Free) oil analysis of microcapsule suspensions

| Sample ID | Capsule Slurry ID | Mass (g) | Hexane (mL) | % Free oil |
|---|---|---|---|---|
| A | Example 4 STPB081318A | 0.262 | 10 | 4.23% |
| B | Example 5 STPB081718A | 0.262 | 10 | 3.32% |
| C | Example 6 STPB081018A | 0.261 | 10 | 5.32% |

TABLE 6-continued

Extractable (or Free) oil analysis of microcapsule suspensions

| Sample ID | Capsule Slurry ID | Mass (g) | Hexane (mL) | % Free oil |
|---|---|---|---|---|
| D | Example 7 STPB090618A | 0.262 | 10 | 2.03% |
| E | Example 8 STPB080118B | 0.256 | 10 | 4.28% |

TABLE 6-continued

Extractable (or Free) oil analysis of microcapsule suspensions

| Sample ID | Capsule Slurry ID | Mass (g) | Hexane (mL) | % Free oil |
|---|---|---|---|---|
| F | Example 9 STPB080618A | 0.258 | 10 | 3.99% |
| G | Perfume Oil, not encapsulated | 0.0125 | 10 | 100% |
| H | Perfume Oil, not encapsulated | 0.0167 | 10 | 100% |
| J | Perfume oil, not encapsulated | 0.025 | 10 | 100% |
| K | Perfume oil, not encapsualted | 0.050 | 10 | 100% |

Example 12. Environmental Biodegradability

Microcapsules of Example 4 and 5 were evaluated for environmental biodegradability by adapting the OCDE/OECD 301D Closed Bottle Test method. Three liters of water from a fresh river source (Lehigh River, Sand Island Access Point, Bethlehem, Pennsylvania) was filtered through a Whatman 597 (catalog 10311808) filter using a Buchner funnel assembly. The following mineral solutions of Table 7 were made:

TABLE 7

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dihydrate | $Na_2HPO_4$—$2H_2O$ | 33.40 |
| | Ammonium chloride Dissolve in water and bring to 1 L. pH to 7.4 | $NH_4Cl$ | 0.50 |
| B | Calcium Chloride anhydrous OR | $CaCl_2$ | 27.50 |
| | Calcium Chloride dehydrate Dissolve in water and bring to 1 L. | $CaCl_2$—$2H_2O$ | 36.40 |
| C | Magnesium sulfate heptahydrate Dissolve in water and bring to 1 L. | $MgSO_4$—$7H_2O$ | 22.50 |
| D | Iron (III) chloride hexahydrate Dissolve in water and bring to 1 L. | $FeCl_3$—$6H_2O$ | 0.25 |

To 996 mL of the filtered water solution, add 1 mL each of mineral solutions A, B, C, and D. Prepare approximately 500 mL solutions containing the particles to be tested. Fill BOD bottles (500 mL capacity) just past the neck of the bottle. Insert stopper. Store BOD bottles in the dark. Use dissolved oxygen meter (YSI 5000), and YSI5905 Dissolved Oxygen meter probe to measure oxygen at specific time points.

TABLE 8

Sample preparation for biodegradability test

| Samples | Concentration (mg/L) |
|---|---|
| Tap water (no microbes control) | 0 |
| Lehigh River Water (no particles control) | 0 |
| Lehigh River water + Aerosil R812 (negative control) | 5.0 |
| River water + starch (complete biodegradation control) | 5.0 HiCAP 100 |
| River water + particles of Example 5 | 7.9 |
| River water + particles of Example 4 | 7.9 |

The dissolved oxygen measured values as a function of time are tabulated in Table 9 below.

TABLE 9

Measured dissolved oxygen concentration as a function of time

| Sample | Day 0 (mg/L O2) | Day 7 (mg/L O2) | Day 21 (mg/L O2) |
|---|---|---|---|
| Tap Water | 7.46 | 7.29 | 7.68 |
| River Water | 5.12 | 5.09 | 4.79 |
| Aerosil R812 (negative) | 7.27 | 5.26 | 4.81 |
| Starch (positive) | 7.29 | 2.42 | 0.60 |
| Example 5 | 8.08 | 3.70 | 2.98 |
| Example 4 | 8.17 | 4.16 | 3.34 |

One then normalizes the $O_2$ concentration (4.81 represents no degradation, 0.60 represents complete degradation; use these values to determine what level of degradation of the microcapsules).

TABLE 10

Normalized oxygen concentration and Biodegradability %

| Samples | Measured $O_2$ Conc at Day 21 (mg/L) | Degradation | Degradation Index |
|---|---|---|---|
| Tap Water | 7.68 | No Degradation | 0% |
| River Water | 4.79 | | |
| Aerosil R812 (negative) | 4.82 | No Degradation Control | 0% |
| Starch HICAP 100 | 0.60 | 100% Degradation Control | 100% |
| Example 5 | 2.98 | $\frac{(4.82 - 2.98)}{(4.82 - 0.60)}$ | 44% |
| Example 4 River water + particles of Example 4F | 3.34 1.74 | $\frac{(4.82 - 3.34)}{(4.82 - 0.60)}$ | 35% |

350%-44% represents the environmental degradability of the microcapsule particles (each sample run in triplicate).

Example 13—Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of Examples 4 to 9, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 13.1 below.

TABLE 13.1

Hair Condition Formulation

| Components | Ex. I (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18 (Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 14—Shampoo

Selected microcapsules from the above examples are formulated into a rinse-off shampoo formulation as follows: to 90.0 grams of shampoo formulation is added an appropriate amount of microcapsule slurry of Examples 4 to 9, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 14.1, 14.2 and 14.3 below.

TABLE 14.1

Shampoo Formulations of Examples 14A-14C.

| Ingredient | 14A | 14B | 14C |
|---|---|---|---|
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsules | 1.2 | 1.2 | 1.2 |
| Preservatives, pH adjusters | Up to 1% | Up to 1% | Up to 1% |

[1] Mirapol AT-1, Copolymer of Acrylamide (AM) and TRIQUAT, MW = 1,000,000; CD = 1.6 meq./gram; 10% active; Supplier Rhodia
[2] Jaguar C500, MW—500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B. 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

1. Mirapol AT-1, Copolymer of Acrylamide (AM) and TRIQUAT, MW=1,000,000; CD=1.6 meq./gram; active; Supplier Rhodia
2. Jaguar C500, MW–500,000, CD=0.7, supplier Rhodia
3. Mirapol 100S, 31.5% active, supplier Rhodia
4. Sodium Laureth Sulfate, 28% active, supplier: P&G
5. Sodium Lauryl Sulfate, 29% active supplier: P&G
6. Glycidol Silicone VC2231-193C
7. Tegobetaine F-B, 300 active supplier: Goldschmidt Chemicals
8. Monamid CMA, 85 active, supplier Goldschmidt Chemical
9. Ethylene Glycol Distearate, EGDS Pure, supplier Goldschmidt Chemical
10. Sodium Chloride USP (food grade), supplier Morton; note that salt is an adjustable ingredient, higher or lower levels may be added to achieve target viscosity.

TABLE 14.2

Shampoo Formulations of Examples 14D-14F.

| Ingredient | 14D | 14E | 14F |
|---|---|---|---|
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.2 | 1.2 | 1.2 |

[1] Glycidol Silicone
[2] Cyclopentasiloxane: SF1202 available from Momentive Performace Chemicals
[5] Behenyl trimethyl ammonium chloride/Isopropyl alcohol: Genamin™ KMP available Clariant
[6] Cetyl alcohol: Konol ™ series available from Shin Nihon Rika
[7] Stearyl alcohol: Konol ™ series available from Shin Nihon Rika
[8] Methylchloroisothiazolinone/Methylisothiazolinone: Konol ™ CG available from Rohm & Hass
[9] Panthenol: Available from Roche
[10] Panthenyl ethyl ether: Available from Roche 1. Glycidol Silicone
4. Cyclopentasiloxane: SF1202 available from Momentive Performance Chemicals
5. Behenyl trimethyl ammonium chloride/Isopropyl alcohol: Genamin™ KMP available from Clariant
6. Cetyl alcohol: Konol™ series available from Shin Nihon Rika
7. Stearyl alcohol: Konol™ series available from Shin Nihon Rika
8. Methylchloroisothiazolinone/Methylisothiazolinone: Kathon™ CG available from Rohm & Haas
9. Panthenol: Available from Roche
10. Panthenyl ethyl ether: Available from Roche

TABLE 14.3

Shampoo Formulations of Examples 14G and 14H

| Ingredient | 14G | 14H |
|---|---|---|
| Sodium Laureth Sulfate | 10.00 | 10.00 |
| Sodium Lauryl Sulfate | 1.50 | 1.50 |

TABLE 14.3-continued

Shampoo Formulations of Examples 14G and 14H

| Ingredient | Example 14G | Example 14H |
|---|---|---|
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules | 0.30 | 0.30 |
| Citric Acid/Sodium Citrate Dihydrate | PH QS | PH QS |
| Sodium Chloride/Ammonium Xylene Sulfonate | Visc. QS | Visc. QS |
| Water | QS | QS |

1 Jaguar C17 available from Rhodia
2 N-Hance 3269 (With Mol. W. of ~500,000 and 0.8 meq/g) available from Aqulaon/Hercules
3 Viscasil 330M available from General Electric Silicones
4 Gel Networks; See composition in Table 14.4 below. The water is heated to about 74° C. and the Cetyl Alcohol, Stearyl Alchol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

1 Jaguar C17 available from Rhodia

2 N-Hance 3269 (with Mol. W. of ~500,000 and 0.8 meq/g) available from Aqulaon/Hercules 3 Viscasil 330M available from General Electric Silicones 4 Gel Networks; See composition in Table 14.4 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 14.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 15—Lotion

For the examples shown in Table 15 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 15

Lotion Formulations (Examples 15A-15C).

| Ingredient/Property | Example 15A | Example 15B | Example 15C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic $TiO_2$ | | | 0.50 |
| Iron oxide coated Mica | | | 0.65 |
| $TiO_2$ Coated Mica | 1.00 | 1.00 | |
| Fragrance Microcapsules | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

12.5% Dimethicone Crosspolymer in Cyclopentasiloxane. Available from Dow Corning.

2 E.g., TOSPEAR 145A or TOSPEARL 2000. Available from GE Toshiba Silicon.

3 25% Dimethicone PEG-10/15 Crosspolymer in Dimethicone. Available from Shin-Etsu.

4 JEENATE 3H polyethylene wax from Jeen.

5 Stearyl Dimethicone. Available from Dow Corning.

6 Hexamidine diisethionate, available from Laboratoires Serobiologiques.

7 Additionally or alternatively, the composition may comprise one or more other skin care actives, their salts and derivatives, as disclosed herein, in amounts also disclosed herein as would be deemed suitable by one of skill in the art.

Example 16—Antiperspirant/Deodorant

Example 16A of Table 16.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 16.1

Antiperspirant/Deodorant Formulation (Example 16A).

| Ingredient | Example 16A |
| --- | --- |
| Part I: Partial Continuous Phase | |
| Hexamethyldisiloxane[1] | QS |
| DC5200[2] | 1.20 |
| Fragrance | 0.35 |
| Fragrance Capsules | 1.00 |

1 DC 246 fluid from Dow Corning
2 from Dow Corning
3 Standard aluminum chlorohydrate solution Examples 16B to 16E of Table 16.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 16F of Table 16.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 16.2

Antiperspirant/Deodorant Formulations

| | Example | | | | |
| --- | --- | --- | --- | --- | --- |
| Ingredient | 16B | 16C | 16D | 16E | 16F |
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.055 | |
| sodium hydroxide | 0.04 | 0.04 | 0.04 | 0.04 | |
| triclosan | 0.3 | 0.3 | 0.3 | 0.3 | |
| Fragrmce | 0.5 | 0.5 | 0.5 | 0.5 | 0.5 |
| Fragrance capsules | 1.0 | 1.0 | 1.0 | 1.0 | 0.5 |
| Propellant (1,1 difluoroethane) | | | | | 40 |

QS—indicates that this material is used to bring the total to 100%.

TABLE 16.1-continued

Antiperspirant/Deodorant Formulation (Example 16A).

| Ingredient | Example 16A |
| --- | --- |
| Part II: Disperse Phase | |
| ACH (40% solution)[4] | 40.00 |
| propylene glycol | 5.00 |
| Water | 12.30 |
| Part III: Structurant Plus Remainder of Continuous Phase | |
| FINSOLVE TN | 6.50 |

QS—indicates that this material is used to bring the total to 100%.
[1]DC 246 fluid from Dow Corning
[2]from Dow Corning
3 Standard aluminum chlorohydrate solution QS—indicates that this material is used to bring the total to 100%.

Example 17—Rinse-Off Conditioner

The conditioning compositions of Examples 17A through 17F of Table 17 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 17B of Table 17 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 20

Rinse-Off Conditioner Formulations (Examples 17A-17F).

| Ingredient | 17A | 17B | 17C | 17D | 17E | 17F[3] |
|---|---|---|---|---|---|---|
| Premix | | | | | | |
| Aminosilicone-1 [1] | 0.50 | 0.50 | | | | |
| Aminosilicone-2 [2] | | | 0.50 | 0.50 | 0.50 | |
| PDMS | | | | | | 0.50 |
| Fragrance microcapsules | ... | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 m mol/g and a viscosity of 3,000-8,000 mPa·s, which is water insoluble
[2] Aminosilicone-1 (TAS): having an amine content of 0.04-0.06 m mol/g and a viscosity of 10,000-16,000 mPa·s, which is water insoluble
[3] Comparative example with PDMS instead of amino silicone 1 Aminosilicone-1 (AMD): having an amine content of 0.12-0.15 m mol/g and a viscosity of 3,000-8,000 mPa·s, which is water insoluble
2 Aminosilicone-2 (TAS): having an amine content of 0.04-0.06 m mol/g and a viscosity of 10,000-16,000 mPa·s, which is water insoluble
3 Comparative example with PDMS instead of amino silicone Example 18—Body Cleansing Composition The body cleaning compositions of Examples 18A-18C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The Benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 18

Body Cleansing Composition Formulations (Examples 18A-18).

| Ingredient | 18A | 18B | 18C |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules | 10 | 10 | 10 |
| III: Surfactant Phase:Benefit Phase Blending Ratio | 50:50 | 90:10 | 90:10 |

Example 19—Fabric Softening Product

Non-limiting examples of product formulations containing purified perfume microcapsules of the aforementioned examples are summarized in the following table.

TABLE 19

Fabric Softening Product Formulations (Examples 19A-19J).

| Ingredient | 19A | 19B | 19C | 19D | 19E | 19F | 19G | 19H | 19I | 19J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 10.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |

TABLE 19-continued

Fabric Softening Product Formulations (Examples 19A-19J).

| Ingredient | 19A | 19B | 19C | 19D | 19E | 19F | 19G | 19H | 19I | 19J |
|---|---|---|---|---|---|---|---|---|---|---|
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculyn™ 44.
*Suitable microcapsules provided in Examples 4 to 9. (Percent active relates to the core content of the microcapsule)

* Suitable microcapsules provided in Examples 4 to 9. (Percent active relates to the core content of the microcapsule)

Example 20—Dry Laundry Formulations

Non-limiting examples of product formulations containing purified perfume microcapsules of the aforementioned examples are summarized in the following table.

TABLE 20

Dry Laundry Formulations (Examples 20A-20G)

| Ingredient | 20A | 20B | 20C | 20D | 20E | 20F | 20G |
|---|---|---|---|---|---|---|---|
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |

TABLE 20-continued

Dry Laundry Formulations (Examples 20A-20G)

| Ingredient | % w/w granular laundry detergent composition Example | | | | | | |
|---|---|---|---|---|---|---|---|
| | 20A | 20B | 20C | 20D | 20E | 20F | 20G |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Examples 4 to 9) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS—as used herein indicates that this material is used to bring the total to 100%.

Example 21—Liquid Laundry Formulations (HDLs)

Non-limiting examples of product formulations containing purified perfume microcapsules of the aforementioned examples are summarized in Tables 21.1, 21.2 and 21.3 below.

TABLE 21.1

Liquid Laundry Formulations (HDLs)

| Ingredient | Example | | | | | |
|---|---|---|---|---|---|---|
| | 21A | 21B | 21C | 21D | 21E | 21F |
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |

TABLE 21.1-continued

Liquid Laundry Formulations (HDLs)

| Ingredient | 21A | 21B | 21C | 21D | 21E | 21F |
|---|---|---|---|---|---|---|
| Perfume Microcapsules of Examples 4 to 9 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 21.2

Liquid Laundry Detergent Formulations

| Ingredient | 21G | 21H | 21I | 21J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |
| Bentonite Softening Clay | | 1.0 | | |
| Polyquaternium 10-Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | 1.0 | |
| Perfume micro capsules (expressed as perfume oil) of Example 4 to 9 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 21.3

Liquid Laundry Detergent Formulations.

| Ingredient | 21K | 21L | 21M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Examples 4 to 9 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 22—Liquid and Gel Detergents

Non-limiting examples of product formulations containing purified perfume microcapsules of the aforementioned examples are summarized in Table 22 below.

TABLE 22

Liquid and Gel Detergent Formulations (% by Weight)

| Ingredient | 22A | 22B | 22C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |

TABLE 22-continued

Liquid and Gel Detergent Formulations (% by Weight)

| Ingredient | 22A | 22B | 22C |
|---|---|---|---|
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Examples 4 to 9 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

Example 23—Liquid Unit Dose

The following are examples of unit dosage forms wherein the liquid composition is enclosed within a PVA film. The preferred film used in the present examples is Monosol M8630 76 μm thickness.

TABLE 23

Unit Dose Laundry Cleaner

| | 23A 3 compartments | | | 23B 2 compartments | | 23C 3 compartments | | |
|---|---|---|---|---|---|---|---|---|
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | 0.4 | | | |
| Brightener | 0.2 | 0.2 | 0.2 | 0.3 | | 0.3 | | |
| Microcapsules Example 4 to 9 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine)[2] | To pH 8.0 for liquids To RA > 5.0 for powders | | | | | | | |
| Solvents (1,2 propandiol, ethanol), sodium sulfate | To 100 p | | | | | | | |

[1] Polyethylenimine (MW = 600) with 20 ethoxylate groups per -NH.
[2] RA = Reserve Alkalinity (g NaOH/dose)

While the invention has been described in detail and with reference to specific examples thereof, it will be apparent to one skilled in the art that various changes and modifications can be made therein without departing from the spirit and scope thereof.

What is claimed is:

1. A composition comprising controlled release particles, wherein each of the controlled release particles comprises:
   (a) a core comprising at least one hydrophobic active ingredient; and
   (b) a wall at least partially surrounding the core and comprising:
      (i) an outer layer comprising a reaction product of an amine and an isocyanate;
      (ii) an intermediate layer under the outer layer and comprising a reaction product of an acid and an isocyanate;
      (iii) an inner layer under the intermediate layer and comprising an acrylate copolymer; and optionally
      (iv) an optional outer layer above the outer layer and comprising a quaternary amine containing moiety,
   wherein the core is switchable from a low viscosity liquid to a semisolid without using high melting point waxes or polymers, and the controlled release particles are effective to retain the at least one hydrophobic active ingredient upon exposure to water and effective to release the at least one hydrophobic active ingredient in response to friction.

2. The composition of claim 1, wherein the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

3. The composition of claim 1, wherein the amine is at least one member selected from the group consisting of linear aliphatic amines, aromatic amines, silicone amines, branched amines, polyamines and amino acids.

4. The composition of claim 1, wherein the isocyanate is at least one member selected from the group consisting of aliphatic isocyanates, aromatic isocyanates, polymeric isocyanates, cyclic isocyanates, hydrophilic isocyanates, hydrophobic isocyanates, waterborne isocyanates and urethane acrylates containing isocyanate functionalities.

5. The composition of claim 1, wherein the acid is an oil soluble acid monomer or oligomer comprising acid acrylates containing more than one carboxylic acid group, or a water soluble acid having more than one carboxylic acid group.

6. The composition of claim 1, wherein the acrylate copolymer is a member selected from the group consisting of ethylene glycol dimethacrylate, diethylene glycol dimethacrylate, aliphatic urethane diacrylates, aromatic urethane diacrylates, difunctional urethane acrylates, ethoxylated aliphatic difunctional urethane methacrylates, aliphatic urethane dimethacrylates, aromatic urethane dimethacrylates, epoxy acrylates, epoxymethacrylates, tetraethylene glycol dimethacrylate, polyethylene glycol dimethacrylate, 1,3 butylene glycol diacrylate, 1,4-butanediol dimethacrylate, 1,4-butaneidiol diacrylate, diethylene glycol diacrylate, 1,6 hexanediol diacrylate, 1,6 hexanediol dimethacrylate, neopentylglycol diacrylate, polyethylene glycol diacrylate, tetraethylene glycol diacrylate, triethylene glycol diacrylate, 1,3 butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, ethoxylated trimethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate.

7. The composition of claim 1, wherein the controlled release particles have a diameter from 0.1 microns to less than 200 microns.

8. The composition of claim 1, which is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

9. The composition of claim 8, further comprising at least one suspension agent to suspend the controlled release particles, wherein the at least one suspension agent is at least one member selected from the group consisting of a rheology modifier, a structurant and a thickener.

10. The composition of claim 9, wherein the at least one suspension agent has a high shear viscosity at, 20 $sec^{-1}$ shear rate and at 21° C., of from 1 to 7000 cps and a low shear viscosity, at 0.5 $sec^{-1}$ shear rate at 21° C., of greater than 1000 cps.

11. The composition of claim 9, which is a fluid having a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

12. The composition of claim 9, wherein the at least one suspension agent is selected from the group consisting of polyacrylates, polymethacrylates, polycarboxylates, pectin, alginate, gum arabic, carrageenan, gellan gum, xanthan gum, guar gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

13. The composition of claim 1, comprising two different controlled release particles which are friction-triggered release microcapsules configured to release the at least one hydrophobic active ingredient at different rates due to a difference in a viscosity of the core.

14. The composition of claim 1, comprising friction-triggered release microcapsules and water-triggered release microcapsules.

15. The composition of claim 1, wherein the at least one hydrophobic active ingredient comprises a mixture of a hydrophobic active and a material selected from the group consisting of brominated oils, epoxidized oils, highly nonpolar oils, hydrophobically modified inorganic particles, nonionic emulsifiers, oil thickening agents.

16. The composition of claim 1, which has an Environmental Biodegradability greater than 30% as measured according to protocol OECD 301D.

17. The composition of claim 1, wherein the controlled release particles include the optional outer layer.

18. A method for preparing the composition of claim 1, said method comprising the steps of:

(a) preparing an oil phase comprising the at least one hydrophobic active ingredient, at least one isocyanate, at least one acrylate, at least one initiator, at least one oil soluble acid, and optionally at least one acrylamide;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) reacting the at least one isocyanate with acidic monomers or oligomers or copolymers to form the intermediate layer comprising a carbamic-carboxylic anhydride;
(e) adding an amine moiety containing material at a stoichiometric ratio from 1:2 to 3:4 to react with the at least one isocyanate for 2-3 hours at room temperature to provide the outer layer;
(f) increasing a temperature at least 5° C. above an initiation temperature and reacting for 2 to 5 hours the at least one acrylate to provide the inner layer defining the core;
(g) adding surface modification agents to a suspension of the controlled release particles to improve adhesion between the particles and intended substrates; and
(h) adding structuring agents to the suspension of the controlled release particles to homogeneously suspend the particles in an aqueous dispersion.

19. A method for preparing the composition of claim 1, said method comprising the steps of:
(a) preparing an oil phase comprising the at least one hydrophobic active ingredient, at least one isocyanate, at least one acrylate, at least one initiator, at least one oil soluble acid, and optionally at least one acrylamide;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) adding an amine moiety containing material at a stoichiometric ratio from 1:2 to 3:4 to react with the at least one isocyanate for 2-3 hours at room temperature to provide the intermediate layer;
(e) adding a water soluble acid and reacting for 2-3 hours at room temperature the at least one isocyanate with acidic monomers or oligomers or copolymers to form a carbamic-carboxylic anhydride outer layer;
(f) increasing a temperature at least 5° C. above an initiation temperature and reacting for 2 to 5 hours the at least one acrylate to provide the inner layer defining the core;
(g) adding surface modification agents to a suspension of the controlled release particles to improve adhesion between the particles and intended substrates; and
(h) adding structuring agents to the suspension of the controlled release particles to homogeneously suspend the particles in an aqueous dispersion.

20. The method of claim 18, wherein the acrylamide is an alkylidene-bis-acrylamide where the alkylidene group has up to four carbon atoms.

21. The method of claim 18, wherein the initiator is a member selected from the group consisting of peroxide, dialkyl peroxide, alkyl peroxide, peroxyester, peroxycarbonate, peroxyketone, peroxydicarbonate, 2,2'-azobis (isobutylnitrile), 2,2'-azobis (2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl)peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethylhexanoate, t-butyl peroxy-2-ethylhexanoate, t-butyl peroxyacetate, di-t-amyl peroxyacetate, t-butyl peroxide, di t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3.3-di-(t-butylperoxy)-butyrate, t-amyl perbenzoate, t-butyl perbenzoate and ethyl 3,3-di-(t-amylperoxy)-butyrate.

22. The method of claim 18, wherein the emulsifier is a member selected from the group consisting of palmitamidopropyltrimonium chloride, distearyl diimonium chloride, cetyltrimethylammonium chloride, quaternary ammonium compounds, fatty amines, aliphatic ammonium halides, alkyldimethyl benzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethylaminoethyl methacrylate), poly(acrylamide-co-diallyldimethylammonium chloride), poly(allylamine), polybis(2-chloroethyl)ether-alt-1,3-bis(3-(dimethylamino)propylurea quaternized, poly(dimethylamine-co-epichlorohydrin-co-ethylenediamine), polyalkylene glycol ether, polyvinyl acetate, copolymers of polyvinyl acetate, polyacrylamide, poly(N-isopropylacrylamide), poly (2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene), polyvinyl pyrrolidone, copolymers of polyvinyl pyrrolidone, 1H-Imidazolium, 1-ethenyl-3-methyl-, chloride, polymer with 1-ethenyl-2-pyrrolidinone, vinyl acetate and gum arabic.

* * * * *